United States Patent
Seal et al.

(10) Patent No.: US 8,916,199 B1
(45) Date of Patent: Dec. 23, 2014

(54) INHIBITION OF ANGIOGENESIS ASSOCIATED WITH OVARIAN CANCER BY NANOPARTICLES OF CERIUM OXIDE

(75) Inventors: Sudipta Seal, Oviedo, FL (US); Ajay Karakoti, Richland, WA (US); Vijayalakshmi Shridhar, Rochester, MN (US); Shailendra Giri, Rochester, MN (US)

(73) Assignee: University of Central Florida Research Foundation, Ind., Orlando, FL (US)

( * ) Notice: Subject to any disclaimer, the term of this patent is extended or adjusted under 35 U.S.C. 154(b) by 488 days.

(21) Appl. No.: 13/182,522

(22) Filed: Jul. 14, 2011

Related U.S. Application Data

(63) Continuation-in-part of application No. 12/429,650, filed on Apr. 24, 2009.

(60) Provisional application No. 61/125,602, filed on Apr. 25, 2008.

(51) Int. Cl.
*A61K 9/14* (2006.01)

(52) U.S. Cl.
USPC .......................................................... 424/489

(58) Field of Classification Search
CPC .......... A61K 33/24; A61K 33/00; A61K 9/14
USPC .......................................................... 424/489
See application file for complete search history.

(56) References Cited

U.S. PATENT DOCUMENTS

| | | | |
|---|---|---|---|
| 5,089,860 A | 2/1992 | Deppe et al. | |
| 5,411,647 A | 5/1995 | Johnson et al. | |
| 5,486,359 A | 1/1996 | Caplan et al. | |
| 5,910,311 A | 6/1999 | Boussourira | |
| 5,961,993 A | 10/1999 | Boussourira | |
| 6,042,714 A | 3/2000 | Lin et al. | |
| 6,103,247 A | 8/2000 | Boussourira | |
| 6,139,985 A | 10/2000 | Borglum et al. | |
| 6,316,012 B1 | 11/2001 | N'Guyen et al. | |
| 6,327,074 B1 | 12/2001 | Bass et al. | |
| 6,368,577 B1 | 4/2002 | Kropf et al. | |
| 6,406,685 B1 | 6/2002 | Philippe | |
| 6,468,551 B1 | 10/2002 | Diec | |
| 6,497,863 B1 | 12/2002 | Wachter | |
| 6,497,865 B1 | 12/2002 | Griesbach | |
| 6,501,590 B2 | 12/2002 | Bass et al. | |
| 6,592,746 B1 | 7/2003 | Schmid-Schoenbein et al. | |
| 6,654,161 B2 | 11/2003 | Bass et al. | |
| 6,844,387 B2 | 1/2005 | Bass et al. | |
| 6,890,896 B1 | 5/2005 | Shashoua | |
| 7,005,504 B2 | 2/2006 | Hsei et al. | |
| 7,075,707 B1 | 7/2006 | Rapaport et al. | |
| 7,141,227 B2 | 11/2006 | Chan | |
| 7,270,813 B2 | 9/2007 | Shimp et al. | |
| 7,347,987 B2 | 3/2008 | McGinnis et al. | |
| 7,431,758 B2 | 10/2008 | Ota et al. | |
| 7,442,686 B2 | 10/2008 | Lasko et al. | |
| 7,471,706 B2 | 12/2008 | Bass et al. | |
| 7,504,356 B1 | 3/2009 | Self et al. | |
| 7,507,480 B2 | 3/2009 | Sugama | |
| 7,534,453 B1 | 5/2009 | Zigaliznski | |
| 7,563,459 B2 | 7/2009 | Phillips et al. | |
| 7,642,250 B2 | 1/2010 | Williams | |
| 7,687,505 B2 | 3/2010 | Sugaya | |
| 7,718,261 B2 | 5/2010 | Katusic et al. | |
| 7,772,375 B2 | 8/2010 | Greferath et al. | |
| 7,888,119 B2 | 2/2011 | Sugaya et al. | |
| 7,899,093 B1 | 3/2011 | Bass et al. | |
| 7,906,147 B2 | 3/2011 | Hainfield | |
| 7,924,617 B2 | 4/2011 | Yip | |
| 8,080,420 B2 | 12/2011 | Sugaya | |
| 8,097,270 B2 | 1/2012 | Ketelson et al. | |
| 8,172,901 B2 | 5/2012 | Altman et al. | |
| 2003/0050709 A1 | 3/2003 | Noth et al. | |
| 2003/0187077 A1 | 10/2003 | Chane-Ching | |
| 2003/0228277 A1 | 12/2003 | Gehlsen | |
| 2004/0013658 A1 * | 1/2004 | Fulton et al. | 424/94.1 |
| 2004/0048808 A1 * | 3/2004 | Hamdi et al. | 514/25 |
| 2004/0062753 A1 | 4/2004 | Rezania et al. | |
| 2005/0159820 A1 | 7/2005 | Yoshikawa et al. | |
| 2005/0164377 A1 | 7/2005 | Miyabayashi et al. | |
| 2005/0171192 A1 | 8/2005 | Gehlsen | |
| 2006/0110440 A1 | 5/2006 | Sugaya | |

(Continued)

FOREIGN PATENT DOCUMENTS

| | | |
|---|---|---|
| WO | WO 99/15891 | 4/1999 |
| WO | WO 03/059263 A2 | 7/2003 |

(Continued)

OTHER PUBLICATIONS

Drisko, J. A. et al. The Use of Antioxidants with First-Line Chemotherapy in Two Cases of Ovarian Cancer, J Am Coll Nut, 2003, 22 (2), 118-123.*

Karakoti, A. S. et al. Nanoceria as Antioxidant: Synthesis and Biomedical Applications, JOM, 2008, 60 (3), 33-37.*

Lecapentier, E et al., "Bevacizumab—induced small bowel perforation in a patient with breast cancer without intraabdominal metastases", 2010, Invest New Drugs, vol. 29, pp. 1500-1503.

Randall, LM et al, "Bevacizumab toxicities and their management in ovarian cancer", 2010, Gynecol Oncol, vol. 117, pp. 497-504.

Sokolov, et al. ,"Real-time vital optical imaging of precancer using anti-epidermal growth factor receptor antibodies conjugated to gold nanoparticles." Cancer Res. 2003, vol. 63:1999, 2004.

Niu, J., et al. "Cardiovascular effects of cerium oxide nanoparticles in a transgenic murine model of cardiomyopathy," Cardiovas. Res. Nov. 30, 2006, Nov. 2006, vol. 73, No. 3, pp. 549-559.

(Continued)

*Primary Examiner* — Gina C Justice
*Assistant Examiner* — Genevieve S Alley
(74) *Attorney, Agent, or Firm* — Timothy H. Van Dyke; Beusse, Wolter, Sanks & Maire, P.A.

(57) ABSTRACT

The invention provides a method of treating ovarian cancer in a mammal, the method inhibits angiogenesis associated with the cancer and comprises the parenteral administration to the mammal of an effective amount of cerium oxide nanoparticles having a predominance of $Ce^{+3}$.

9 Claims, 12 Drawing Sheets

(56) References Cited

U.S. PATENT DOCUMENTS

| | | | |
|---|---|---|---|
| 2006/0134789 | A1 | 6/2006 | Sugaya et al. |
| 2006/0141137 | A1 | 6/2006 | Anderson et al. |
| 2006/0280729 | A1 | 12/2006 | Mistry |
| 2007/0003621 | A1 | 1/2007 | Nagia et al. |
| 2007/0072825 | A1 | 3/2007 | Williams |
| 2007/0123996 | A1* | 5/2007 | Sugaya et al. ............. 623/23.51 |
| 2009/0087493 | A1 | 4/2009 | Dai et al. |
| 2009/0098574 | A1 | 4/2009 | Brisson et al. |
| 2009/0269410 | A1* | 10/2009 | McGinnis et al. ............. 424/489 |
| 2010/0098768 | A1 | 4/2010 | Andreescu et al. |
| 2010/0151000 | A1 | 6/2010 | Thomas et al. |
| 2010/0247428 | A1 | 9/2010 | Kim et al. |

FOREIGN PATENT DOCUMENTS

| | | |
|---|---|---|
| WO | WO 2006/118954 A2 | 11/2006 |
| WO | WO 2007/002662 A2 | 1/2007 |
| WO | 2008064357 A2 | 5/2008 |
| WO | WO 2008/064357 A2 | 5/2008 |
| WO | WO 2009/132277 A1 | 10/2009 |

OTHER PUBLICATIONS

Qureshi, M.A., et al. "Increased exhaled nitric oxide following autologous peripheral hemotopietic stem cell transplantation; a potential marker of idopathic pneumonia syndrome," Chest, Jan. 2004, vol. 125, No. 1, pp. 281-287.

Ohgushi, et al., "Stem Cell Technology and Bioceramics: From Cell to Gene Engineering", J. Biomed. Mat. Res. 48: 913-927; 1999.

Dal Maschio, et al., "Influence of Ce3+/Ce 4+ ratio on phase stability and residual stress field in ceria-yttria stabilized zirconia plasma-sprayed coatings", J. Mat. Sci. 27: 5591-5596; 1992.

Ramsfjell, et al., "Distinct Requirements for Optimal Growth and In Vitro Expansion of Human CD341CD382 Bone Marrow Long-Term Culture-Initiating Cells (LTC-IC), Extended LTC-IC, and Murine In Vivo Long-Term Reconstituting Stem Cells", Blood 99: 4093-4102; 1999.

Devasenpathi, et al., "Forming near net shape free-standing components by plasma spraying", Mat. Let. 57: 882-886; 2002.

Imamura, et al. "Drusen, choridal neovascularization and retinal pigment epithelium dysfunction in SOD1-deficient mice: A model of age-related macular degeneration," PNAS, vol. 103, No. 30; 11282-11287 (Jul. 25, 2006).

Hollyfield, et al. "Oxidative damage-induced inflammation initiates age-related macular degeneration," Nature Medicine, vol. 14, pp. 194-198 (2008).

Birch, et al. Age-related macular degeneration: a target for nanotechnology derived medicines. International Journal of Nanomedicine, 2007, 2(1), 65-77.

Maulik, N. Reactive oxygen species drives myocardial angiogenesis? Antioxidants & Redox Signaling, 2006, 8(11-12) 2161-2168.

Kuchibhatla et al., "Hierarchical assembly of inorganic nanostructure building blocks to octahedral superstructures a true template-free self-assembly", Nanotechnology, 2007, vol. 18, pp. 1-4.

Ohia, et al. "Pharmacological consequences of oxidative stress in ocular tissues," Mutation Research, 2005, 579, 22-36.

Liu, et al. "Subtype lesions of neovascular age-related macular degeneration in Chinese paitents," Braefe's Arch Clin Exp Opthalmol, 2007, 245, 1441-1445.

Silva. "Seeing the benefits of ceria," Nature Nanotechnology, 2006, 1, 92-94.

Hahn, et al. "Maculas affected by Age-Related Macular Degeneration Contain Increased Chelatable Iron in the Retinal Pigment Epithelium and Bruch's Membrane," Arch. Opthalmol. 2003, 121, 1099-1105.

Haywood, et al. "Inflammation and Angiogenesis in Osteoarthritis," Arthritis & Rheumatism, 2003, 48 (8), 2173-2177.

Chen, et al. Rare Earth Nanoparticles Prevent Retinal Degeneration Induced by Intracellular Peroxides: Nature Nano Technology, 1(2) 142-148 (2006).

Moongkarndi, et al. "Antiproliferation, antioxidation and induction of apoptosis by *Garcinia mangostana* (mangosteen) on SKBR3 human breat cancer cell line," J. of Ethno-Pharmacology, vol. 90, (2004) pp. 161-166.

Margrain, et al. "Do blue light filters confer protection against age-related macular degeneration?", Progress in Retinal and Eye Research, vol. 23 (2004) pp. 523-531.

Bailey, et al. "Cerium Oxide Nanoparticles Extend Cell Longevity and Act as Free Radical Scavengers," online (retrieved on Apr. 24, 2006) from: http://www.med.miami.edu/mnbws/Rzigalinski11.html.

Tsai, Ming-Shyong. "The Study of the synthesis of nano-grade cerium oxide powder," Materials Letters 58, 2270-2274 (2004).

Rzigalinski, Beverly Ann, et al. "Cerium Oxide nanoparticles increase the lifespan of cultured brain cells and protect against free radical mechanical trauma" FASEB Journal, vol. 17 No. 4-5, Page Abstract No. 377.24 URL, XP008095016 & FASEB Meeting on Experimental Biology: Translating the Genome, San Diego, CA USA, Apr. 11-15, 2003 ISSN: 0892-6638 *Abstract*.

Cook, et al. "Neuronal Damage induced by polychlorinated biphenyls is partically reversed by cerium oxide nanoparticles" [online] vol. 2003, 2003, XP008095032 Retrieved from the internet: URL http://sfn.scholarone.com/itin2003/main.htm]?new_page_id=126&abstract_id=126&abstract_id=14513&p_num=669.13&is_tech=0> [retrieved on May 8, 2008] *abstract*.

Tusnekawa, S., et al. "Lattice relaxation of monosize Ce02-x nanocrystalline particles" Applied Surface Science Elsevier Netherlands, vol. 152, No. 1-2, Nov. 1999, pp. 53-56.

Hooper, Claire, Y., et al. "New treatment in age-related macular degeneration" Clinical & Experimental Opthalmology, Oct. 2003, pp. 376-391.

Qi, et al. "Redispersible Hybrid Nanopowders; Cerium Oxide Nanoparticle complexes with Phosphonated-PEG Oligomers," ACS Nano, 2008, vol. 2(5), pp. 879-888.

Otsuka, et al. "PEGylated nanoparticles for biological and pharmaceutical applications," Advanced Drug Delivery Reviews, 2003, vol. 55, pp. 403-419.

Olivier, et al. "Synthesis of pegylated immunonanoparticles." Pharmaceutical Research, Aug. 2002, vol. 19, No. 8, pp. 1137-1143.

Shui, Y.B., et al. "Morphological observation on cell death an dphagocytosis induced by ultraviolent irradiation in a cultured human lens epithelial cell line," Dec. 2000, vol. 71, pp. 609-618.

Xijuan, et al. "Size-dependent optical properties of nanocrystalline Ce02:Er obtained by combustion synthesis," Sep. 24, 2001, Phys. Chem. Chem Phys., vol. 3, pp. 5266-5269.

Guo, "Green and red upconversion luminescence in Ce02:Er3+ powders produced by 785 nm laser," Jounral of Solid State Chemistry 180, p. 127-131, 2007.

Perez, J. M., et al. "Synthesis of Biocompatible Dextran-Coated Nanoceria with pH-Dependent Antioxidant Properties," Small, vol. 4 No. 5, 2008, pp. 552-556.

Pirmohamed, et al. "Nanoceria exhibit redox state-dependent catalase mimetic activity," Chem. Comm, 2010, 46, pp. 2736-2738.

Nazem, et al. "Nanotechnology for Alzheimer's disease detection and treatment." Insciences J., 2011, vol. 1(4), pp. 169-193.

Karakoti, et al. "Direct Synthesis of Nanoceria in Aqueous Polyhydroxyl Solutions." J. Phys. Chem. C, vol. 111, No. 46, 2007, pp. 17232-17240.

Tarnuzzer, et al. "Vacancy Engineered Ceria Nanostructures for Protection from Radiation-Induced Cellular Damage," Nano Lett, vol. 4, No. 12, pp. 2573-2577, 2005.

Heckert, et al. "The role of cerium redox state in the SOD mimetic activity of nanoceria," Biomaterials, 29, 2008, pp. 2705-2709.

Schubert, et al. "Cerium and yttrium oxide nanoparticles are neuroprotective," Feb. 2006, Biochemical and Biophysical Research Communications, 342, p. 86-91.

Zhang, et al. Cerium oxide nanoparticles: size selective formation and structure analysis, Jan. 2002, Applied Physics Letters, vol. 81, No. 1, p. 127-129.

Patil, et al. "Surface-derived nanoceria with human carbonic anhydrase II inhibitors and flourphores: a potential drug delivery device." J. Phys. Chem. C., 2007, vol. 111, No. 24, pp. 8437-8442.

(56) References Cited

OTHER PUBLICATIONS

Patil, et al. "Synthesis of nanocrystalline ceria particles for high temperature oxidation resistant coating," Journal of Nanoparticle Research, 2002, vol. 4: ppl. 433-438.
Jin, et al. "Nanopartical-mediated drug delivery and gene therapy," Biotechnol. Prog, 2007, vol. 23, pp. 32-41.
Eck, et al. "PEGylated gold nanoparticles conjugated to monoclonal F19 antibodies as targeted labeling agents for human pancreatic carcinoma tissue," ACS Nano, 2008, vol. 2(11) pp. 2263-2272.
Nafee. Dissertation entitled "Cationically-modified nanoparticles for the polmonary delivery of the telomerase inhibitor 2'-O-Methyl RNA for the treatment of lung cancer," Dissertation zur Erlangung des Grades des Doktors der, Naturwissenschaftern der Naturwissenschaftilch—Technischen Fakul't III Chemie, Pharmazie, Bio-und Werstoffwissenschaften der Universit des Saarlandes, 2008 ****.
Suh et al., "Multifunctional nanosystems at the interface of physical and life sciences", Nano Today, 2009, vol. 4, pp. 27-36.
Suzuki et al., "Preparation and characteristics of magnetite labelled antibody with the use of poly(ethylene glycol) derivatives", Biotechnol. Appl. Biochem., 1995, vol. 21, pp. 335-345.
Monte et al., "Inhibition of lymphocyte induced angiogenesis by free radical scavengers", Free Radic Biol Med, 1994, vol. 17, pp. 259-266.
Buettner, et al., "Ascorbate (vitamin C, It's Antioxidant Chemistry", Presentation, 2002.
PCT/US2011/0044329; PCT International Search Report and Written Opinion, Dec. 8, 2011.
Drisko, J.A. et al., "The use of Antioxidants with First-Line Chemotherapy in Two Cases of Ovarian Cancer", J Am Coll Nut, 2003, vol. 22(2), pp. 118-123.
Korsvik et al., "Superoxide dismutase mimetic properties exhibited by vacancy engineered ceria nanoparticles", Chem. Commun., 2007, pp. 1056-1058.
Yu et al., "Large-scale nonhydrolytic sol-gel synthesis of uniform-sized ceria nanocrystals with spherical, wire, and tadpole shapes", Angew. Chem. Int. Ed., 2005, vol. 44, pp. 7411-7414.
Ahluwalia et al., "Critical role of hypoxia sensor—HIF1 alpha in VEGF gene activation, implication for angiogenesis and tissue injury healing", Current Medicinal Chemistry, 2012, vol. 19, p. 94.
Perez, J.M. et al., "Synthesis of Biocompatible Dextran-Coated Nanoceria with pH-Dependent Antioxidant Properties", 2008, Small, vol. 4, No. 5, pp. 552-556.
Griffiths, J.R., "Are Cancer Cells Acidic?", British Journal of Cancer, 1991, vol. 64, pp. 425-427.
De Wever, O. et al., "Stromal myofibroblasts are drivers of invasive cancer growth", International Journal of Cancer, 2008, vol. 123, pp. 2229-2238.
Lam, M.A., et al., "Nitric Oxide and Nitroxides Can Act as Efficient Scavengers of Protein-Derived Free Radicals", Chem Res. Toxicol, 2008, vol. 21, pp. 2111-2119.
Karakoti, A.S., et al., "Nanoceria as Antioxidant: Synthesis and Biomedical Applications", JOM, 2008, vol. 60(3), pp. 33-37.
Clinicaltrials.gov, "Clinical Trial for the Treatment of Diabetic Foot Ulcers Using a Nitric Oxide Releasing Patch: PATHON", (http://web.archive.org/web/20091130234819/http://clinicaltrials.gov/show/NCT/00428727) published online Nov. 30, 2009.
Deshpande et al., "Size dependency variation in lattice parameter and valency states in nanocrystalline cerium oxides", Appl;ied Physics Letters, 2005, vol. 87, pp. 133113-1-3.
Rasmussen et al., "Penetration of intact skin by quantum dots with diverse physiochemical properties", Toxicological Sciences, 2006, vol. 91, pp. 159-165.
Park et al., "Oxidative stress induced by cerium oxide nanoparticles in cultured BEAS-2B cells", Toxicology, 2008, vol. 245, pp. 90-100.
MSDS from Aldrich for cerium oxide powder bulk product, Feb. 2013, 6 pages.
Kuchibhatla, S. et al., "Hierarchicial assembly of inorganic nanostructure building blocks to octahedral superstructures—atrue template-free self-assembly", Nanotechnology, 2007, vol. 17 pp. 1-4.

Kuchibhatla, S, "Probing and Tuning the Size, Morphology, Chemistry and Structure of Nanoscale Cerium Oxide", Diss. University of Central Florida, 2008, 175 pages.
Girt, S et al., "Nanoceria: A Rare-Earth Nanoparticle as a Novel Anti-Angiogenic Therapeutic Agent in Ovarian Cancer", PLOS ONE, Jan. 2013, vol. 8, Issue 1, e54578.
Dong et al., "Activation of glassy carbon electrodes by dispersed metal oxide particles", J. Electrochem Soc., 1984, pp. 813-819.
Bast RC, Jr. et al, "Early detection of ovarian cancer: promise and reality", 2002, Cancer Treat Res vol. 107, pp. 61-97.
Friedlander, ML, "Prognostic factors in ovarian cancer", 1998, Semin Oneal, vol. 25, pp. 305-314.
Chen, J et al;, "Rare earth nanoparticles prevent retinal degeneration induced by intracellular peroxides", 2006, Nat Nanotechnol, vol. 1, pp. 142-150.
Das, M, et al, , "Auto-catalytic ceria nanoparticles offer neuroprotection to adult rat spinal cord neurons", 2007, Biomaterials, vol. 28, pp. 1918-1925.
Tarnuzzer, RW et al., "Vacancy engineered ceria nanostructures for protection from radiation-induced cellular damage", 2005, Nano Lett vol. 5, pp. 2573-2577.
Patil, S et al, "Protein adsorption and cellular uptake of cerium oxide nanoparticles as a function of zeta potential", 2007, Biomaterials, vol. 28, pp. 4600-4607.
Carmeliet, P et al., "Angiogenesis in cancer and other diseases", 2000, Nature, vol. 407, pp. 249-257.
Kerbel, R et al., "Clinical translation of angiogenesis inhibitors", 2002, Nat Rev Cancer, vol. 2, pp. 727-739.
Ferrara, N, "Vascular endothelial growth factor", 1996, Eur J Cancer, vol. 32A, pp. 2413-2422.
Macchiarini, P. et al, "Relation of neovascularisation to metastasis of non-small-celllung cancer", 1992, Lancet, vol. 340, pp. 145-146.
Paley, PJ et al., "Vascular endothelial growth factor expression in early stage ovarian carcinoma", 1997, Cancer, vol. 80, pp. 98-106.
Weidner, N. et al, "Tumor angiogenesis correlates with metastasis in invasive prostate carcinoma", 1993, Am J Pathol, vol. 143, pp. 401-409.
Weidner, N et al., "Tumor angiogenesis and metastasis—correlation in invasive breast carcinoma", 1991, N Engl J Med, vol. 324, pp. 1-8.
Burger, RA et al., "Phase II trial of bevacizumab in persistent or recurrent epithelial ovarian cancer or primary peritoneal cancer: a Gynecologic Oncology Group Study", 2007, J Clin Oncol, vol. 25, pp. 5165-5171.
Narita, K et al, "HSulf-1 inhibits angiogenesis and tumorigenesis in vivo", 2006, Cancer Res, vol. 66, pp. 6025-6032.
Rattan, R et al., "Metformin attenuates ovarian cancer cell growth in an AMP-kinase dispensable manner", 2011, J Cell Mol Med. vol. 15, pp. 166-178.
Rattan, R et al., "5-Aminoimidazole-4- carboxamide-1-beta-D-ribofuranoside inhibits cancer cell proliferation in vitro and in vivo via AMP-activated protein kinase", 2005, J Bioi Chern, vol. 280, pp. 39582-39593.
Giri, S et al., "The role of AMPK in psychosine mediated effects on oligodendrocytes and astrocytes: implication for Krabbe disease", 2008, J Neurochem, vol. 105, pp. 1820-1833.
Giri, S et al., "Krabbe disease: psychosine-mediated activation of phospholipase A2 in oligodendrocyte cell death", 2006, J Lipid Res, vol. 47, pp. 1478-1492.
Malinda, KM et al., "Thymosin beta4 accelerates wound healing", 1999, J Invest Dermatol, vol. 113, pp. 364-368.
Rattan, R et al., "Metformin suppresses ovarian cancer growth and metastasis with enhancement of cisplatin cytotoxicity in vivo", 2011, Neoplasia in Press.
Chan, OW et al, "Loss of MKP3 mediated by oxidative stress enhances tumorigenicity and chemoresistance of ovarian cancer cells", 2008, Carcinogenesis, vol. 29, pp. 1742-1750.
Liu, LZ et al., "Reactive oxygen species regulate epidermal growth factor-induced vascular endothelial growth factor and hypoxia-inducible factor-1alpha expression through activation of AKT and P70S6K1 in human ovarian cancer cells", 2006, Free Radic Bioi Med, vol. 41, pp. 1521-1533.

(56) References Cited

OTHER PUBLICATIONS

Xia, C et al., "Reactive 1o oxygen species regulate angiogenesis and tumor growth through vascular endothelial growth factor", 2007, Cancer Res vol. 67, pp. 10823-10830.

Miyamoto, S et al., "New approach to cancer therapy: heparin binding-epidermal growth factor-like growth factor as a novel targeting molecule", 2007, Anticancer Res, vol. 27, pp. 3713-3721.

Gomez-Raposo, C et al., "Angiogenesis and ovarian cancer", 2009, Clin Transl Oncol, vol. 11, pp. 564-571.

Markman, M, "Antiangiogenic drugs in ovarian cancer", 2009, Expert Opin Pharmacother, vol. 10, pp. 2269-2277.

Lose, F et al., "Vascular endothelial growth factor gene polymorphisms and ovarian cancer survival", 2010, Gynecol Oneal, vol. 119, pp. 479-483.

Mesiano, S et al., "Role of vascular endothelial growth factor in ovarian cancer: inhibition of ascites formation by immunoneutralization", 1998, Am J Pathol, vol. 153, pp. 1249-1256.

Tempfer, C et al., "Vascular endothelial growth factor serum concentrations in ovarian cancer", 1998, Obstet Gynecol, vol. 92, pp. 360-363.

Xu, L et al., "Interleukin 8: an autocrine growth factor for human ovarian cancer", 2000, Oncol Res, vol. 12, pp. 97-106.

Takahashi, T et al., "A single autophosphorylation site on KDR/Fik-1 is essential for VEGF-A-dependent activation of PLC-gamma and DNA synthesis in vascular endothelial cells", 2001, Embo J, vol. 20, pp. 2768-2778.

Kroll, J et al., "The vascular endothelial growth factor receptor KDR activates multiple signal transduction pathways in porcine aortic endothelial cells", 1997, J Bioi Chern, vol. 272, pp. 32521-32527.

Bharali, OJ et al., "Emerging nanomedicines for early cancer detection and improved treatment: current perspective and future promise", 2010, Pharmacal Ther, vol. 128, pp. 324-335.

Seigneuric, R et al., "From nanotechnology to nanomedicine: applications to cancer research", 2010, Curr Mol Med, vol. 10, pp. 640-652.

Colon, J et al., "Protection from radiation-induced pneumonitis using cerium oxide nanoparticles", 2009, Nanomedicine, vol. 5, pp. 225-231.

Colon, J et al., "Cerium oxide nanoparticles protect gastrointestinal epithelium from radiation-induced damage by reduction of reactive oxygen species and upregulation of superoxide dismutase 2", 2010, Nanomedicine vol. 6, pp. 698-705.

Amin, KA et al., "The protective effects of cerium oxide nanoparticles against hepatic oxidative damage induced by monocrotaline", 2011, Int J Nanomedicine, vol. 6, pp. 143-149.

Alili, L et al., "Combined cytotoxic and anti-invasive properties of redox-active nanoparticles in tumor-stroma interactions", 2011, Biomaterials, vol. 32, pp. 2918-2929.

Hardas, SS et al., "Brain distribution and toxicological evaluation of a systemically delivered engineered nanoscale ceria", 2010, Toxicol Sci, vol. 116, pp. 562-576.

Folkman, J "Tumor angiogenesis: therapeutic implications:", 1971, N Engl J Med. vol. 285, pp. 1182-1186.

Cross, MJ et al., "VEGF receptor signal transduction", 2003, Trends in Biochem Sci, vol. 28, No. 9, pp. 488-494.

Ushio-Fukai M, et al., "Reactive oxygen species and angiogenesis: NADPH oxidase as target for cancer therapy", 2008, Cancer Lett, vol. 266, pp. 37-52.

Burger, RA, "Overview of anti-angiogenic agents in development for ovarian cancer", 2011, Gynecol Oncol, vol. 121, pp. 230-238.

Cannistra, SA et al., "Phase II study of bevacizumab in patients with platinum-resistant ovarian cancer or peritoneal serous cancer", 2007, J Clin Oncol, vol. 25, pp. 5180-5186.

Garcia, AA et al., "Phase II clinical trial of bevacizumab and low-dose metronomic oral cyclophosphamide in recurrent ovarian cancer: a trial of the California, Chicago, and Princess Margaret Hospital phase II consortia", 2008, J Clin Oncol, vol. 26, pp. 76-82.

Penson, RT et al., "Phase II study of carboplatin, paclitaxel, and bevacizumab with maintenance bevacizumab as first-line chemotherapy for advanced mullerian tumors", Jan. 2010, J Clin Oncol vol. 28, pp. 154-159.

Bansal,N et al., "Bladder perforation in a patient with recurrent epithelial ovarian cancer after treatment with bevacizumab", 2011, Gynecol Oncol, vol. 120, pp. 313-314.

Koskas, M et al., "Wound complications after bevacizumab treatment in patients operated on for ovarian cancer", 2010, Anticancer Res, vol. 30, pp. 4743-4747.

\* cited by examiner

FIGURE 3
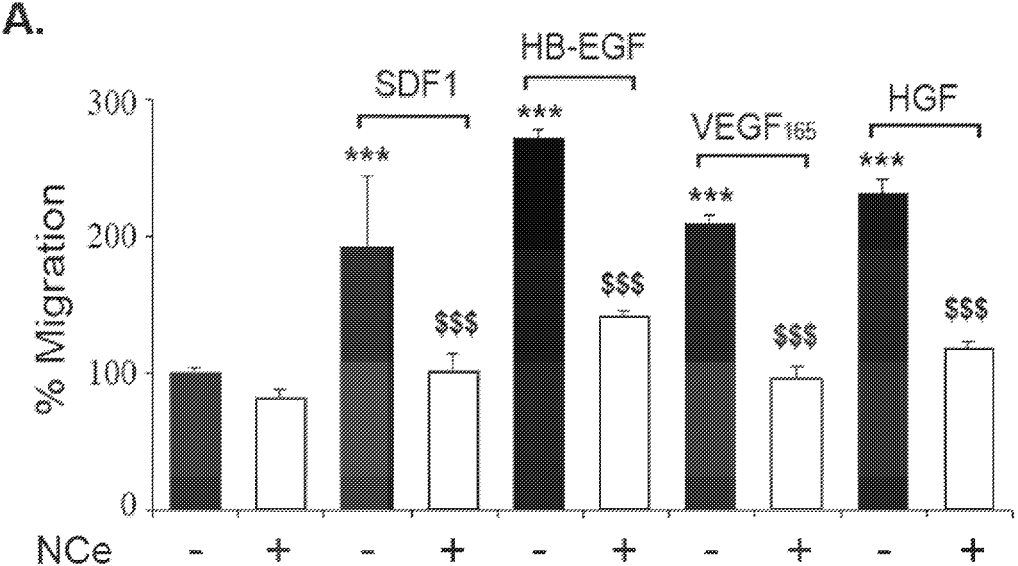
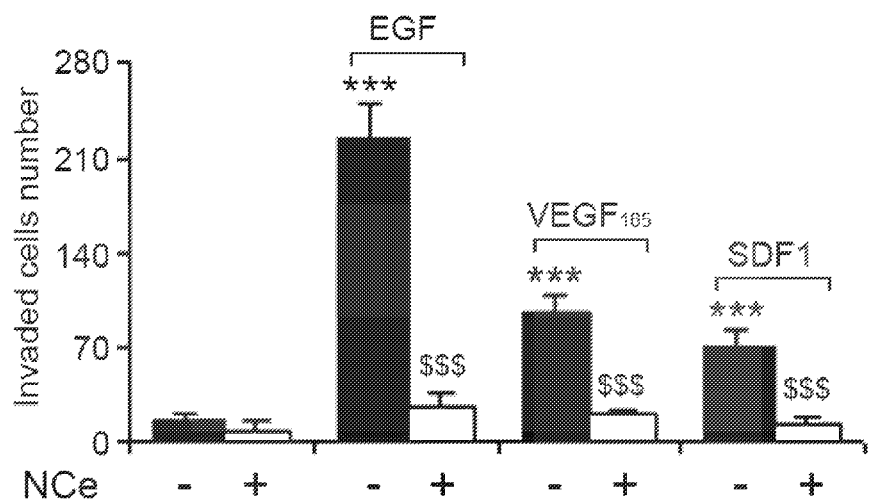

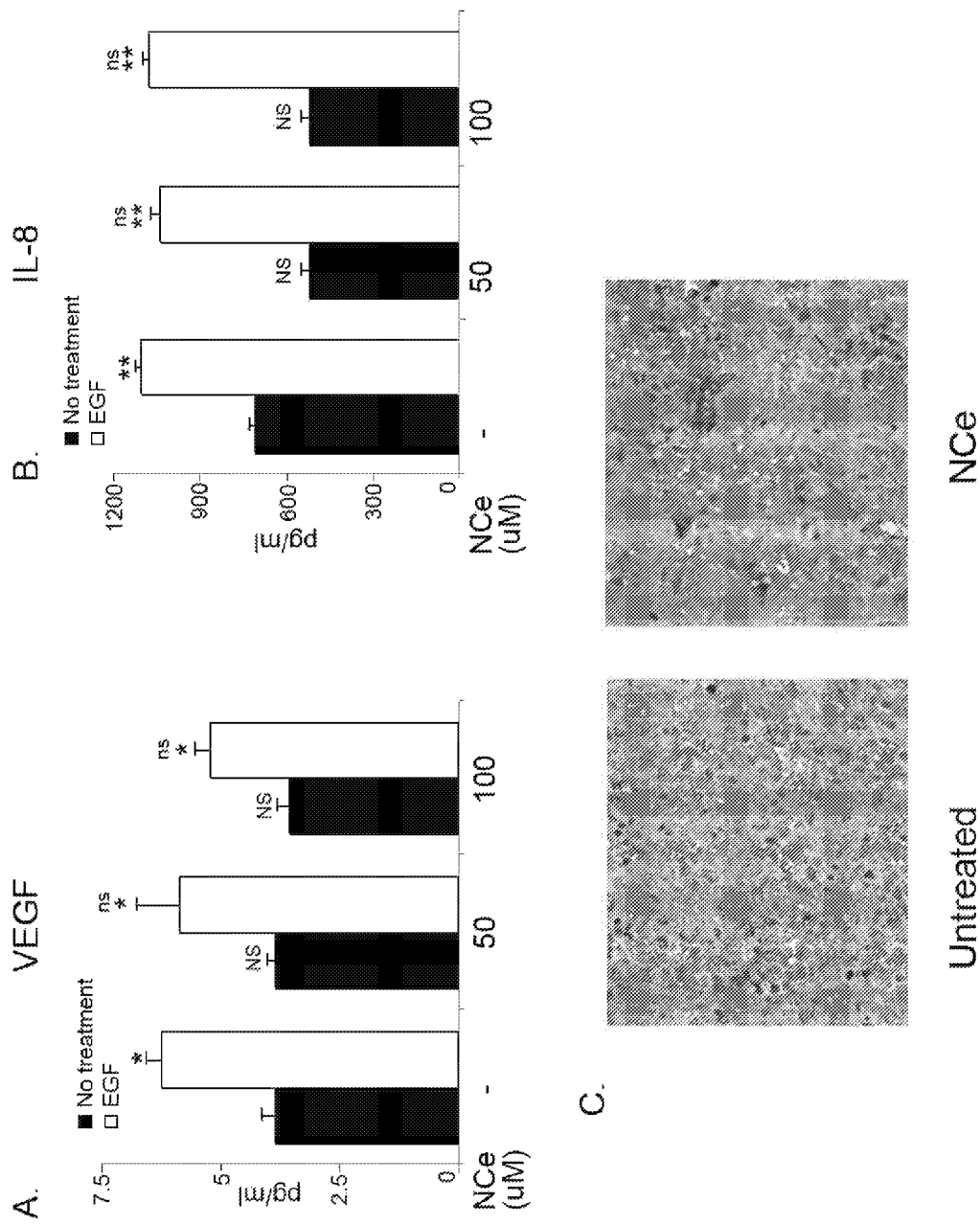

INHIBITION OF ANGIOGENESIS ASSOCIATED WITH OVARIAN CANCER BY NANOPARTICLES OF CERIUM OXIDE

RELATED APPLICATION

This application is a continuation-in-part of and claims priority from co-pending nonprovisional application Ser. No. 12/429,650, which was filed on 24 Apr. 2009, claiming priority to provisional application Ser. No. 61/125,602, filed on 25 Apr. 2008, both of which are incorporated herein by reference in their entirety.

STATEMENT OF GOVERNMENT RIGHTS

The invention claimed herein was made with at least partial support from the U.S. Government. Accordingly, the government may have certain rights in the invention, as specified by law.

FIELD OF THE INVENTION

The present invention relates to the field of cancerous diseases and, more particularly, to nanoparticles of cerium oxide and their use in a treatment which inhibits angiogenesis associated with the cancer.

BACKGROUND OF THE INVENTION

In the United States, 27,000 women are newly diagnosed and approximately 14, 000 women die from ovarian cancer (OvCa) annually [1]. Such high mortality rates are due to majority of patients (75%) presenting with advanced (stage III or greater) disease at the time of diagnosis [2]. More than 90% of the patients have better prognosis if the cancer is detected in its earliest stages. Treatment of epithelial ovarian cancer generally involves surgical debulking followed by chemotherapy with a combination of platinum and a taxane-containing agent. However, majority of patients recur and ultimately succumb to their cancer. Consequently, there is a vast need to develop new therapeutics that can be more effective in treating ovarian cancer and delaying or preventing recurrences. Novel therapies that target ovarian tumorigenesis are extensively been researched, but we have yet to come up with a promising drug.

Nanotechnology based tools and techniques are rapidly emerging in the fields of medical imaging and targeted drug delivery. Cerium oxide is a rare-earth oxide that is found in the lanthanide series of the periodic table. Nanocrystalline cerium oxide (nanoceria) exhibits a blue shift in the ultraviolet absorption spectrum, the shifting and broadening of Raman allowed modes and lattice expansion as compared to bulk cerium oxide indicating its unique properties. Nanoparticulate cerium oxide, also known as nanoceria or NCe, has emerged as a fascinating and lucrative material in biomedical science due to its unique ability to switch oxidation states between (III) and (IV) depending upon the environment. The ability to switch between mixed oxidation states of nanoceria is comparable to biological antioxidants. This imparts nanoceria with a very important biological property of radical scavenging which can be tuned based upon the retention of oxygen vacancies (defects) and concentration of $Ce^{3+}$ species in nanoceria. The reversibility of oxidation state is the key property in making nanoceria a potent antioxidant, thereby eliminating the need for repeated dosage. Previous studies have demonstrated that cerium oxide nanoparticles possess excellent antioxidant properties and act as potent, regenerative free radical scavengers in biological systems [3,4,5]. These regenerative antioxidant properties are due, in part, to the valence structure of the cerium atom combined with inherent defects in the crystal lattice structure, which are magnified at the nano scale. It has been suggested that the unique structure of engineered cerium oxide nanoparticles, with respect to valence and oxygen defects, promotes cell longevity and decreases toxic insults by virtue of its antioxidant effects that occur when the nanoparticles enter the cells [6] preventing the accumulation of reactive oxygen species (ROS) in cell [3].

Tumor angiogenesis is characterized by the formation of new, irregular blood vessels from a preexisting vascular network. This abnormal angiogenesis is required for the growth, survival, and metastasis of most solid tumors [7,8]. Vascular endothelial growth factor (VEGF) is one of the most important proangiogenic factors, which acts as a mitogen for vascular endothelial cells in vitro and as an angiogenic factor in vivo [9]. It is over expressed in various human cancers [10, 11, 12, 13] including ovarian cancer. Recently it has been suggested that ROS played an important role in regulating tumor induced angiogenesis by controlling VEGF production. Enhanced production of VEGF has been shown to correlate with a poor outcome for patients with both early and advanced OvCa. Various anti-angiogenic agents have been and are undergoing evaluations in ovarian cancer clinical trials. A phase II study of single-agent bevacizumab (a monoclonal antibody directed against VEGF) showed promising results [14]. Therefore, VEGF signaling is becoming the focus of antiangiogenesis-targeted therapies in ovarian cancer.

The present disclosure concerns the novel approach of using cerium oxide nanoparticles as a therapeutic agent for ovarian cancer treatment. Our data demonstrate that NCe was able to curtail ovarian cancer growth, migration and invasion and its main mechanism of action appears to be via inhibition of angiogenesis by targeting the endothelial cells

SUMMARY OF THE INVENTION

Ovarian cancer is the fifth most common cause of death among women in the U.S. and the leading cause of death from gynecological malignancies. There is an urgent need for novel therapies to counteract the high mortality rate associated with OvCa. We have developed and engineered nanoparticles of cerium oxide for a potential nanotherapeautic for ovarian cancer treatment. Here, we show for the first time that the NCe attenuated growth factor (SDF1, HB-EGF, VEGF165 and HGF) induced cell migration and invasion of SKOV3 cells, without affecting the cell proliferation. For investigating the preclinical in vivo therapeutic potential of NCe, human A2780 ovarian cancer cells were injected intraperitoneally in nude mice and NCe (0.1 mg/kg body weigh) was administered intra-peritoneally every third day for 4 weeks. NCe treated mice showed significant reduction (p<0.002) in the tumor growth accompanied by decreased tumor cell proliferation as evident from the tumor size and Ki67 staining. Reduction of the tumor mass was accompanied by attenuation of angiogenesis, as observed by reduced CD31 staining and CD31 positive count in xenografts from treated mice. Further examination of NCe's anti-angiogenic property, revealed that NCe inhibited $VEGF_{165}$ induced proliferation, capillary tube formation and activation of VEGFR2 and MMP2 in human umbilical vascular endothelial cells. Collectively, these results indicate that cerium oxide based NCe is a novel nanoparticle that can potentially be used as an anti-angiogenic therapeautic agent in ovarian cancer With the foregoing in mind, the present invention advantageously provides a method of treating ovarian cancer in a mammal, the method comprising parenteral administration to the mammal of an effective amount of cerium oxide nanoparticles having a predominance of Ce$^{+3}$. The mammal is preferably a human subject. Parenteral administration of the cerium oxide nanoparticles is a preferred route of administration, particularly intraperitoneal administration. In the method, an effective amount comprises less than approximately 1 mg per kilogram of body weight of the mammal and most preferably comprises approximately 0.1 mg per kilogram of body weight of the mammal. In the method, the effective amount is preferably parenterally administered approximately every 72 hours.

Alternate embodiments of the invention include a method of inhibiting mammalian ovarian cells, the method comprising contacting the cells with an effective amount of cerium oxide nanoparticles having a predominance of Ce$^{+3}$. Another embodiment includes a method of inhibiting angiogenesis associated with a mammalian ovarian carcinoma, the method comprising contacting the carcinoma with an effective amount of cerium oxide nanoparticles having a predominance of Ce$^{+3}$. Contacting the carcinoma preferably comprises contacting vascular endothelial cells associated with the carcinoma.

The invention additionally discloses a composition of matter comprising nanoparticles of cerium oxide wherein Ce$^{3+}$ predominates over Ce$^{4+}$. The nanoparticles preferably comprise a particle size of from approximately 25 μM to approximately 50 μM and wherein Ce$^{3+}$ predominates over Ce$^{4+}$.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which:

FIG. 3: Illustrates that NCe treatment attenuated cell migration and invasion in ovarian cancer cell. A. Effect of NCe on various growth factors mediated cell migration was examined using wound closure assay as described in Material and Methods. Percent migration was calculated by measuring the length and the width of the cell free area. The width was measured at three different points along the scratch area and then averaged to get an accurate representation of the entire scratch. Percent migrated area was determined by using the formula [area at 0 time/area+GF]×100. Results are shown as mean±S.D. of n=7. B. To examine effect of NCe on invasion, 1×10$^5$ SKOV3 cells were seeded into the upper wells with 100 μM NCe in the FIA chamber in 500 μl culture medium. Various growth factors (EGF, VEGF$_{165}$ and SDF1) (25 ng/ml) was added to the underlying media. 24 hrs later, invasion was determined following manufacturer's instructions. Results are shown as mean±S.D. of triplicates. ***p<0.001 growth factor treated compared to control. $$$p<0.001 NCe treated compared to growth factor.

FIG. 12: NCe does not affect the production of VEGF and IL8 in SKOV3 cells. SKOV3 cells were plated and kept under serum free conditions overnight before being stimulated by EGF. Post 24 h supernatant was collected to perform ELISA. A. VEGF levels. B. IL18 levels. *p<0.01, **p<0.001 of EGF treated to no treatment. NS=non-significant NCe treated to untreated; ns=non-significant NCe/EGF treated to EGF treated C. Representative photomicrograph of VEGF staining (400×) in A2780 xenografts at day 30

DETAILED DESCRIPTION OF THE PREFERRED EMBODIMENT

Figure 1:
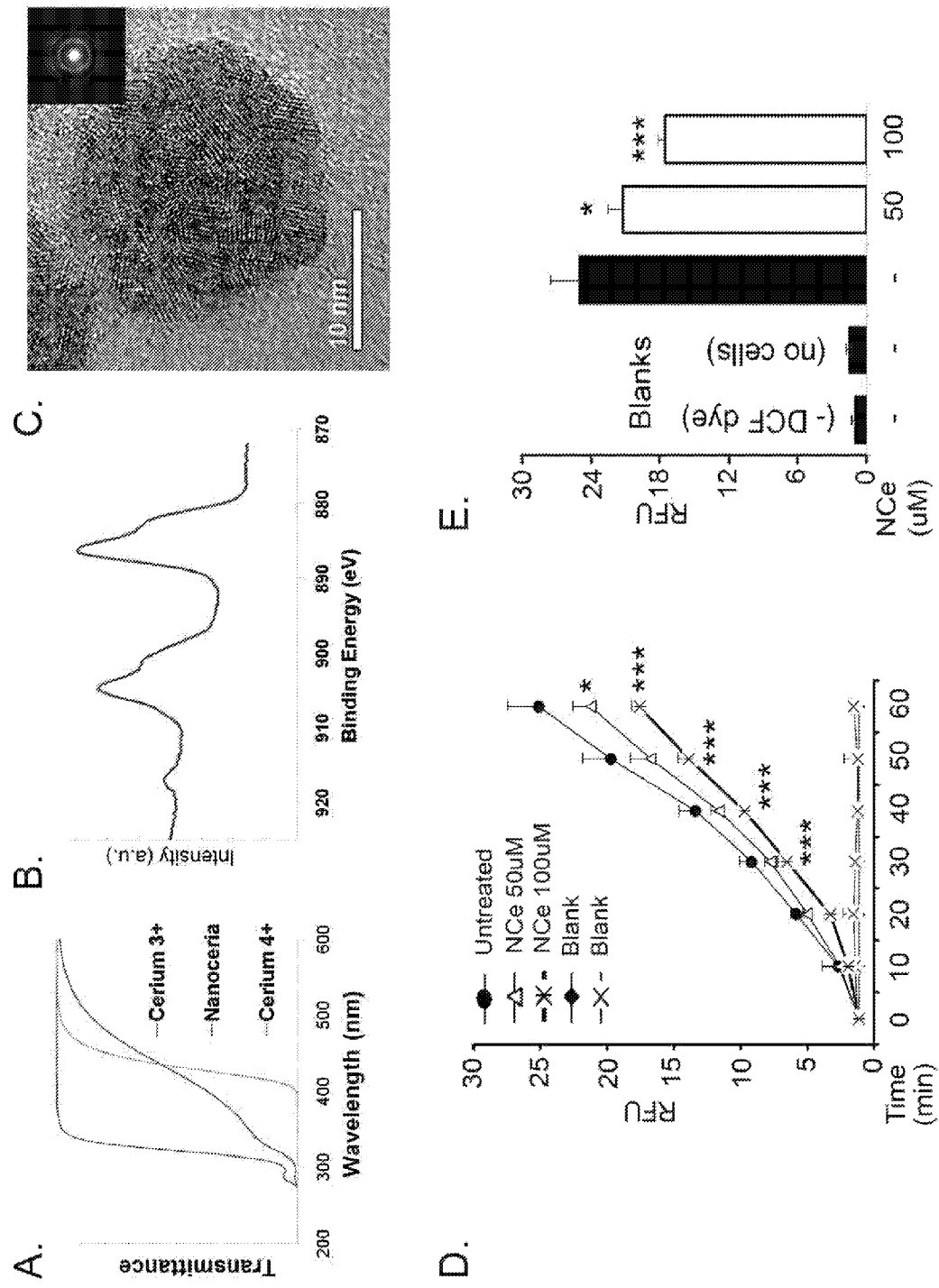
FIG. 1 Shows Preparation and characterization of NCe. A. UV-visible graph of ceria nanoparticles taken after one week of aging (cerium 3+ and cerium 4+ transmission plots are shown for reference); B. XPS spectrum of ceria nanoparticles showing the binding energy region of cerium and proves the presence of both cerium (III) and cerium (IV) species. The peaks between 875 to 895 eV belong to Ce 3d5/2 degenerate levels; C. High resolution transmission electron micrograph of ceria nanoparticles showing the presence of individual 3-5 nm particles in 10-15 nm agglomerate. The inset confirms the fluorite structure of nanoceria; D. Basal levels of ROS in ovarian cancer cell line. A2780 cells were treated with NCe (50-100 μM) for 48 h. Cells were washed with PBS and loaded with DCF-DA dye (5 μM) and fluorescence was recorded at excitation 485 nm and emission 530 nm for various time periods (5-60 min). Wells containing only cells without DCFDA dye (cross) or without cells containing DCFDA dye (filled diamond) were used as a blank; E. Bar graph represents ROS levels at the 60 min of treatment with DCF-DA dye. Results are shown as mean±S.D. of 4 samples. ***p<0.001 NCe at 100 μM; *p<0.05 NCe compared to untreated cells.

The present invention will now be described more fully hereinafter with reference to the accompanying drawings, in which preferred embodiments of the invention are shown.

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described below. However, the skilled should understand that the methods and materials used and described are examples and may not be the only ones suitable for use in the invention.

Moreover, it should also be understood that any temperature, weight, volume, time interval, pH, salinity, molarity or molality, range, concentration and any other measurements, quantities or numerical expressions given herein are intended to be approximate and not exact or critical figures unless expressly stated to the contrary. Accordingly, where appropriate to the invention and as understood by those of skill in the art, it is proper to describe the various aspects of the invention using approximate or relative terms and terms of degree commonly employed in patent applications, such as: so dimensioned, about, approximately, substantially, essentially, consisting essentially of, comprising, and effective amount.

Further, any publications, patent applications, patents, and other references mentioned herein are incorporated by reference in their entirety as if they were part of this specification. However, in case of conflict, the present specification, including any definitions, will control. In addition, the materials, methods and examples given are illustrative in nature only and not intended to be limiting.

Accordingly, this invention may be embodied in many different forms and should not be construed as limited to the illustrated embodiments set forth herein. Rather, these illustrated embodiments are provided so that this disclosure will be thorough, complete, and will fully convey the scope of the invention to those skilled in the art. Other features and advantages of the invention will be apparent from the following detailed description, and from the claims.

Materials and Methods
Reagents and Antibodies:

Trypan Blue and MIT 3-(4,5-dimethylthiazol-2-yl)-2,5-diphenyl tetrazolium bromide) and HB-EGF were from Sigma. SDF1, VEGF165 and HGF were purchased from R&D Systems (MN, USA). Ki-67 antibody was purchased from Dako (Glostrup, Denmark) and VEGF antibody was purchased from Abcam (MA, USA). CD31 (PECAM) was from Santa Cruz Biotechnology (CA, USA).

Cell Culture:

Human ovarian cancer cell lines SKOV3 and HUVEC were from American Type Culture Collection. A2780 and C200 cell lines were a kind gift of Dr. Tom Hamilton (Fox Chase Cancer Center). All cell lines were maintained and cultured in complete RPMI media containing 10% FBS, antibiotics. HUVEC cells were maintained in EBM-2 media purchased from Lonza (Denmark).

Nanoparticle Synthesis:

Cerium Oxide nanoparticles were prepared by wet chemical synthesis as described previously {Karakoti, 2007 #30; Karakoti, 2008 #31; Karakoti, 2009 #24}. Briefly, cerium nitrate hexahydrate was dissolved in deionized water and then filtered using a 200 nm filter to get rid of any freely suspending particulates. The solution containing cerium ions was then oxidized using hydrogen peroxide and ammonium hydroxide. The pH of the solution was adjusted between 3.5-4.0 by using nitric acid or ammonium hydroxide. All the glasswares were autoclaved before being used for synthesis. The pH and the zeta potential of the suspension were closely monitored as the solution was allowed age at room temperature for next several days until the formation of nanoparticles with predominantly $Ce^{3+}$ concentration was observed using UV-Visible spectrophotometry.

Nanoparticles Characterization:

Change in the oxidation states of the as-prepared nanoparticles in solution was monitored using UV-Visible spectrophotometry. Aliquots from the parent sample were taken for absorbance measurements by using Perkin Elmer 750 S spectrophotometer. The particle morphology and size distribution was studied using high-resolution transmission electron microscopy (HRTEM). The size of the nanoparticles in as prepared solution prior to use in in-vitro and in-vivo studies was also monitored using dynamic light scattering (DLS). The oxidation states of cerium in particles were confirmed using X-ray photoelectron spectroscopy (XPS). For High Resolution Transmission Electron Microscopy (HRTEM) a drop of suspension of nanoparticles was deposited on the carbon-coated copper grid. The HRTEM images of the as-prepared particles were obtained with a Philips (Tecnai Series) operateing at 300 keV. The XPS data were obtained using a 5400 PHI ESCA (XPS) spectrometer. Samples were drop casted on a silicon wafer and dried inside a nitrogen glove box to avoid the oxidation of cerium from atmospheric oxygen and transferred using a sample transfer chamber without exposing the samples to atmosphere. Only limited scans were obtained to avoid x-ray damage of cerium. An initial scan was saved separately to compare with the combined 5 scan results and showed no difference in the $Ce^{3+}/Ce^{4+}$ ratio. The base pressure during XPS analysis was 10-9 Torr and Mg-Ka X-ray radiation (1253.6 eV) at a power of 200 W was used as x-ray source. The binding energy of Au ($4f_{7/2}$) at 84.0±0.1 eV was used to calibrate the binding energy scale of the spectrometer. Any charging shift produced in the spectrum was corrected by referencing to the C (1 s) position at (284.6 eV) [13]. XPS spectra smoothing and baseline subtraction was carried out using PeakFit (Version 4) software.

Migration and Invasion Assays:

SKOV3 cells were grown in serum-free media overnight. Cell migration and invasion were measured as described [15] with modifications. Briefly, cell suspensions (500 µl, $2.5\times10^4$ cells) were seeded on the top of uncoated (migration assay) and Matrigel-coated (invasion assay) transwell plates (8-µm pore diameter; BD Biosciences). Serum-free cell suspensions (500 µl) were added to the top chamber of the transwell. The lower chambers contained serum free media containing various growth factors including SDF1, HB-EGF, VEGF165 and HGF at the concentration of 25 µg/ml. Cells invading the lower chamber were stained with 0.5% crystal violet (60% PBS, 40% EtOH) and counted with an inverted microscope. The results from at least two independent experiments in triplicate are presented.

Proliferation Assays:

(i) MTT assay: $2.5\text{-}5.0\times10^4$ cells were plated in 24 well plates in triplicates and treated with indicated concentrations of NCe for 72 h. MTT assay was performed as described before [16], to ascertain the number of live cells. (ii) Thymidine assay: Proliferation of cells was also determined by [$^3$H]-thymidine incorporation into DNA as described before [17]. In brief, $2.5\text{-}5.0\times10^4$ cells were plated in 24 well plates in triplicates and treated with indicated concentrations of NCe for 72 h. Each group was treated with 1fÝCi of [$^3$H] thymidine in the same medium for 6 h. The adherent cells were fixed by 5% trichloroacetic acid and lysed in SDS/NaOH lysis buffer. Radioactivity was easured by Beckman LS3801 liquid scintillation counter (Canada).

Colony Formation Assay:

2000 cells were plated in triplicates in 6-well plates and treated with indicated concentrations of NCe. The cells were allowed to form colonies for up to 2-4 weeks (depending on the cell line) and media was replaced every fourth day. Formed colonies were stained with MTT and counted as described before [16].

Measurement of ROS:

ROS were determined using the membrane-permeable fluorescent dye 6-carboxy 2',7'-dichlorodihydrofluorescein diacetate (DCFDA) in serum-free medium as described previously [18,19]. The cultured cells, with or without treatment with NCe, were treated with 5 µM DCF dye in PBS and change in fluorescence was recorded at excitation 485 nm and emission 530 nm for various time period from 10 to 60 min using a Soft Max Pro spectrofluorometer (Molecular Devices, Sunnyvale, Calif.).

Western Blot:

After stipulated time of incubation in the presence or absence of indicated amounts of NCe, and immunoblot analysis with specific antibodies was performed as previously described [16, 17, 18, 19]. In brief, treated and untreated HUVEC cells with VEGF165 (25 ng/ml) and/or NCe at various time period (5-30 min) were lysed in lysis buffer (50 mM Tris-HCl (pH 7.5), 250 mM NaCl, 5 mM EDTA, 50 mM NaF, and 0.5% Nonidet P-40] containing a protease inhibitor cocktail (Sigma). 50 µg of proteins were resolved by SDS-PAGE and transferred onto nitrocellulose membrane. The membrane was then blocked for 1 h in 5% nonfat dry milk TTBS (20 mM Tris, 500 mM NaCl, and 0.1% Tween 20, pH 7.5) and incubated overnight in primary antisera (pVEGFR and β actin) containing 5% nonfat dry milk or 5% BSA in case of phospho-antibodies. Blots were washed with TTBS (four times, 5 min each) and incubated for 45 min at room temperature. HRP-conjugated anti-rabbit or anti-mouse secondary Ab was added at a dilution of 1/5000. The blots were washed three times in TTBS and developed with an ECL detection system (GE Healthcare, Piscataway, N.J.).

In Vitro Vascular Tube Formation Assay:

In vitro tube formation assays were performed as described by Melinda et. al. [20]. In brief, matrigel matrix was uniformly plated onto 8-well chamber slides (0.15 ml) and incubated at 37° C. for 30 min. Trypsinized HUVEC cells suspended in growth factors free medium. The cells were counted and diluted to $2\times10^5$/ml in medium. To set up the tube formation assay, cells were treated with NCe (25-50 µM) and mixed with cells in the presence or absence of VEGF165 (25 ng/ml) and transferred to each well (200 µl) coated with matrigel. The plates or slides were incubated at 37° C. for 16 h and imaged under a phase contrast inverted microscope at 10x objective magnification.

Zymography Assay:

For MMP2 activity, HUVEC cells will be treated VEGF165 (25 ng/ml) in the presence or absence of NCe (25-50 µM). Post 18 h, cell supernatant was collected centrifuged at 12,000 g and 25 µl mixed with 5xSDS loading buffer without reducing agent and ran on 10% tris-glycine gel containing gelatin. Gel was washed twice for 1 h with renaturating solution (2.5% TritonX100® in 50 mM tris pH 7.4, 5 mM CaCl, 1 mM $ZnCl_2$) to remove SDS and renature MMPs. After rinsing gel with deionized water, gel was incubated overnight at 37° C. with 50 mM tris pH 7.4, 5 mM CaCl, 1 mM ZnCl$_2$. Next day, gel was stained with 0.5% Coomassie G250 followed by de-staining to see MMP2 activity in gel.

Animals:

Mice were maintained according to Institutional IACUC-approved protocol. Mice (6-7 weeks old) were randomized into two groups and 2×10$^6$/200 µl cells in PBS were injected into the intraperitoneal cavity (day 0) as described before [21]. NCe treatment at the dose of 0.1 mg/kg body weight began 3 days post inoculation of cells and given intraperitoneally at every 3d day till end of the study. Mice were sacrificed at 4 weeks and tumors were fixed in formalin for sectioning. Blood was collected in heparin to obtain plasma. Liver, kidney, heart and spleen from all animals were formalin fixed and processed. One tumor and organ slide from each mouse was stained with H&E.

Cytotoxicity Assays:

Blood was collected in heparin coated tubes just before mice were sacrificed. Plasma isolated from blood of six mice from each group was subjected to analysis of a panel of liver function tests (aspartate aminotransferase; alanine aminotransferase; albumin) and kidney function tests (creatinine; urea; albumin) as described before [21]. All assays were performed using kits from Bioassay Systems (CA, USA). All assays were performed according to the manufacturer's instructions.

IHC:

Fixed tumors excised from mice were processed for immunohistochemistry for CD31, Ki-67 and TUNEL (Millipore) according to the manufacturer's protocol and described before [21]. H&E staining was performed by Mayo immunohistochemical core facilities. Ki-67 and H&E sections were examined under light microscope and representative pictograms were taken from 5 different slides of each group. For CD31 staining, TRITC-labeled secondary antibody was used and visualized using fluorescent microscope. For double staining, the slides were first processed for CD31 staining followed by an immunofluorescence TUNEL staining protocol according to manufacturer's instructions.

Live Tumor Measurements:

H&E stained xenograft sections were observed by a pathologist. Maximum diameter of viable tumor was calculated by summing the largest uni-dimensional diameter of each fragment of tumor using the Olympus® BX-41 microscope and a micrometer. Similarly, necrotic areas were measured and the composite live tumor size was calculated from each slide.

HUVEC Tube Formation:

Statistical Analysis:

The data were statistically analyzed using two-tailed Student's t-test (Prism) or the Student-Newman-Keuls test (GraphPad Software). *P<0.001; P<0.01,*P<0.05; NS: not significant compared to untreated cells.

Results

Figure 2:
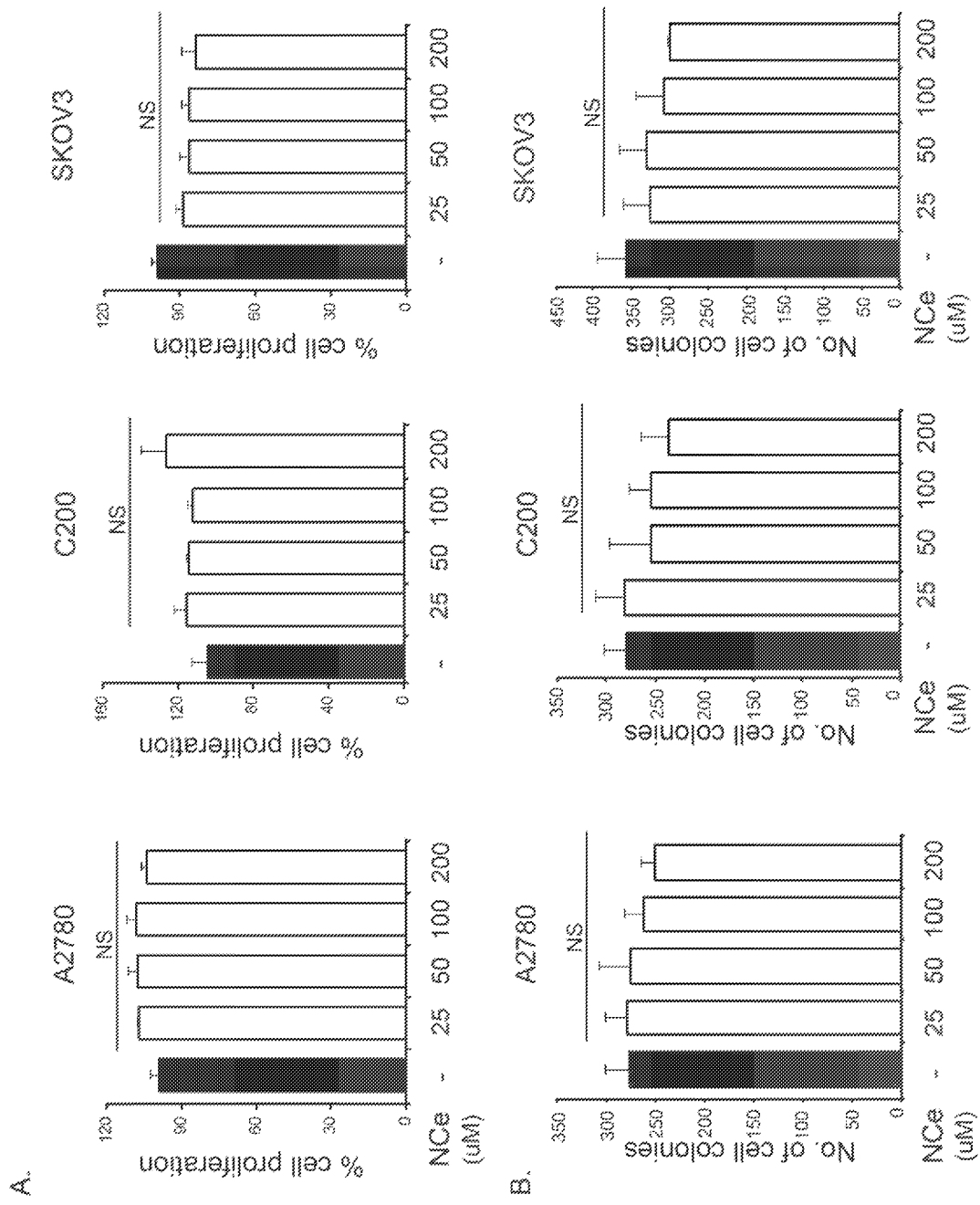
FIG. 2 Shows that NCe treatment did not affect proliferation and colony formation in ovarian cancer cell lines. A. Various ovarian cancer cell lines (A2780, C200 and SKOV3), were plated in 96 well plates (5×10$^4$ cells/well) and treated with indicated doses of NCe (25-200 μM). Post 72 h MTT assay was performed to estimate live cells. The data is plotted as % of control. The data is represents three separate experiments done in triplicates. NS: not significant, compared to untreated cells at respective time point. B. For colony formation, 2000 cells/well (A2780, C200 and SKOV3) were plated in 6-well plates and treated with indicated concentrations of NCe, every third day for 2 weeks until colonies were formed. The colonies were stained with MTT and counted. The data represents three separate experiments done in triplicates. NS: not significant compared to untreated cells.

Synthesis and Characterization of Cerium Oxide Nanoparticles and its Effect on ROS Levels in Ovarian Cancer Cell Line:

As prepared cerium oxide nanoparticles in this study contains individual crystallites of 3-5 nm that are loosely agglomerated to 15-25 nm. As the synthesis process is free from any organic surfactant the hard agglomeration of nanoparticles is controlled by tightly controlling the pH of the nanoparticles below 3.5 during synthesis to keep them in colloidal range. Nanoparticles can be diluted in aqueous or cellular media after the synthesis. FIGS. 1 a and b shows the high resolution transmission electron micrographs (HRTEM) of NCe nanoparticles. It is evident from the image that nanoparticles are loosely agglomerated to about 15-25 nm aggregates which could also be induced by the drying process. The hydrodynamic radius (37.8 nm±0.8) from the multimodal size distribution (volume %) analysis of DLS measurements agrees with the loose agglomerate size of the HRTEM analysis. High magnification image confirms the (111) lattice planes of NCe in individual 3-5 nm crystallites. UV-Visible spectroscopy was used to analyze the oxidation states of cerium oxide nanoparticles before and after aging treatment. FIG. 2 shows the UV-Visible spectra from fresh and aged cerium oxide nanoparticles clearly indicating the predominance of Ce$^{+3}$ oxidation state from the absorption peak at 252 nm as compared to absorption peak at 298 nm for Ce$^{4+}$. Further confirmation on the oxidation states of nanoparticles was obtained from XPS analysis. The XPS spectrum of cerium is very complex that contains multiple peaks from the spin orbit coupling of 3d orbitals {Deshpande, 2005 #10}. Several peaks in the Ce3d region that have been ascribed to 3d$_{3/2}$ (899.5, 900.9, 903.5, 906.4 and 916.6) and 3d$_{5/2}$ (880.2, 882.1, 8885, 888.1 and 898) arising from multiple valence states of cerium. The spectrum from NCe shows a predominance of cerium in +3 oxidation state as depicted by the characteristic peaks at 880.2, 885.0, 899.5 and 903.5 eV. Taken together the data from characterization of NCe is consistent with previous reports wherein cerium can be retained in trivalent oxidation by decreasing the size of the nanoparticles {Deshpande, 2005 #10; Karakoti, 2007 #30; Karakoti, 2008 #31; Karakoti, 2009 #24}.

Cerium oxide nanoparticles, including NCe have been shown to act as a free radical scavengers and as a result by inhibitsing the production of reactive oxygen species (ROS) production [3, 4, 5]. Since, it is well established that ROS accumulation plays an important role in initiation and progression of tumorigenesis in human ovarian cancer [22, 23, 24], we examined the effect of NCe on ROS generation in ovarian cancer cell line. For this, A2780 cell line was treated with NCe (50-100 µM). Post 48 h of treatment, ROS generation was measured using DCFH2-DA dye followed by fluorescence reading. As shown in FIG. 1D-E, NCe treatment significantly inhibited ROS levels in A2780 cell line, suggesting that NCe treatment inhibits basal levels of oxidative stress in ovarian cancer cell line.

Nce Did not Affect Cell Proliferation in Ovarian Cancer Cell Lines:

We further examined the effect of NCe on ovarian cancer growth in vitro. For this, various ovarian cancer cell lines (A2780, C200 and SKOV3) were plated in 96 well plates at 4×10$^3$ cells/well and treated with various concentrations of NCe (25-200 µM). Cell viability was determined at 72 hrs by MTT assay. As shown in FIG. 2A, NCe treatment had no significant effect on the proliferation or survival of ovarian cancer cell lines. To confirm this observation, we also performed clonogenic assay (FIG. 2B) and found similar observation further confirming that NCe did not affect cell proliferation of ovarian cancer cells. To further substantiate these results, we also determined proliferation using [3H] thymidine uptake in A2780, C200 and SKOV3 cells (FIG. S1), observing the same. Similar results were obtained in additional ovarian cancer cell lines including Caov3 and TOV21G (data not shown). Overall, NCe treatment did not significantly inhibit the growth of ovarian cancer cells lines in vitro.

NCe Inhibited Growth Factor-Mediated Cell Migration and Invasion in Vitro:

We further evaluated the effect of NCe on ovarian cancer cell migration and invasion in vitro. For this, we used SKOV3 cells, which are known to migrate and invade proficiently in presence of growth factors (SDF1, HB-EGF, VEGF165 and HGF). Growth factors (GF) have been shown to play important roles in the progression of ovarian cancer including peritoneal dissemination and invasion [25]. SKOV3 cells grown overnight in low serum (0.2%) containing medium were scratched using a sterile 200 μl pipette tip, once they reached 90% confluency. Various growth factors including SDF1, HB-EGF, VEGF165 and HGF (25 μg/ml) were added individually to the medium in the presence or absence of NCe (100 μM). 24 hrs later, the rate of wound closure was calculated. As depicted in FIG. 3A, NCe inhibited all growth factor mediated cell migration in SKOV3 cell line. Similar observation was found in additional ovarian cancer cell lines (A2780 and C200) (data not shown). Next we assessed the effect of NCe in inhibiting GF-mediated invasion of SKOV3 cells using Boyden chamber migration assay (BD Bioscience). FIG. 3B clearly demonstrates that NCe treatment significantly inhibited all growth factors induced invasion of SKOV3 cells compared to untreated cells. Thus, NCe has the ability to inhibit migration and invasion of ovarian cancer cells without effecting their proliferation.

Figure 4:
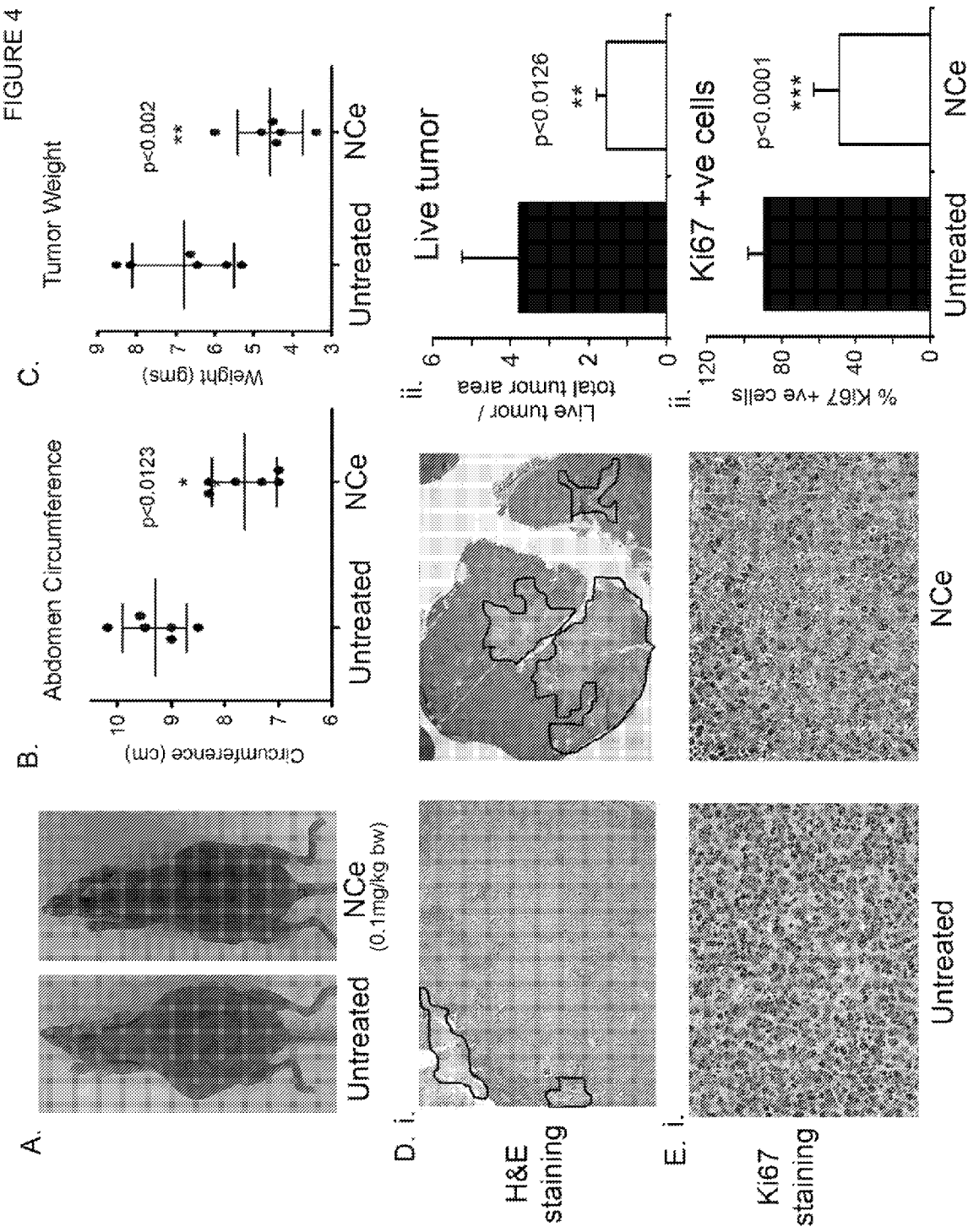
FIG. 4: NCe treatment restricted ovarian tumor growth in vivo. A. Gross morphology of representative mouse with tumors at day 30 (n=6). B Cumulative abdominal circumference at the end of the study. C. Excised tumor weight from vehicle (PBS) treated and NCe (0.1 mg/kg bd wt; every third day). D. (i) Representative H&E (×20) photomicrographs exhibiting live (purple) and necrotic (pink, encircled) areas in untreated and treated xenografts. (ii) Graphical representation of viable tumor size measured as described in Material and Methods. E. (i) Representative Ki-67 staining (×200) of excised A2780 xenografts at day 30. (ii) Count of positive Ki-67 cells from 5 high powered fields (×400) in 3 different xenografts from each group. Counts are expressed as percentage of control.

NCe Treatment Attenuated Tumor Growth in Human A2780 Ovarian Carcinoma Cell Line Bearing Nude Mouse Model:

We further investigated if NCe will be able to restrain in vivo growth and spread of the ovarian cancer using a preclinical mouse model. For this, A2780 cells were injected intraperitoneally (IP) in athymic nu/nu mice to develop ovarian tumors. Mice were treated with NCe (0.1 mg/kg body weight) given intraperitoneally, every third day till end of the study (day 30) as described in the material and methods. FIG. 4A (top panel) shows a representative gross photograph of a NCe treated and untreated mouse bearing A2780 tumor at the end of study (day 30). The abdominal circumference, indicative of the tumor burden in the peritoneum (FIG. 4B) and the tumor weight (FIG. 4C) in the NCe treated mice were significantly ($p<0.002$) reduced compared to untreated mice. The mean weight of the excised tumors was approximately 33% less in NCe (4.56+0.345 gm) treated mice compared to vehicle (PBS) mice (6.79+0.53 gm) (FIG. 4C). This data clearly indicates that NCe has the ability to restrict ovarian tumor growth in vivo when administered at a low dose (0.1 mg/kg).

To examine how NCe affected the tumor growth in vivo, the excised tumor tissue was formalin fixed and processed for immunohisochemical evaluation. Representative H&E staining depicting A2780 tumor morphology is shown in FIG. Di (20×) Observation of H&E sections showed most of the cells to be live in untreated xenografts, while NCe treated had significantly more areas with dead (necrotic) cells (FIG. 4Di; 20×; non-viable area encircled). To quantitate the live and dead areas in the xenograft sections, uni-dimensional measurements of the viable tumor and total tumor size were taken as described in the methods section. As quantitated in FIG. 4Dii, NCe treated tumors had less viable tumor size than the untreated mice. To see the status of proliferation in tumor cells, Ki-67 staining was performed. Significant difference was observed in the number of cells staining positive for Ki-67 (FIG. 4Ei). Enumeration of Ki-67 positive cells counted over 5 high power fields of five sections from each group also showed significant less Ki-67 positive cells in NCe treated xenografts compared to untreated group (expressed in % age; FIG. 4E ii), indicating that less number of cells were proliferating under NCe treatment. Together, this data shows that NCe has the ability to restrict ovarian tumor growth in vivo due to decreased proliferation and increased non-viable tumor mass by an unknown mechanism as yet.

Figure 5:
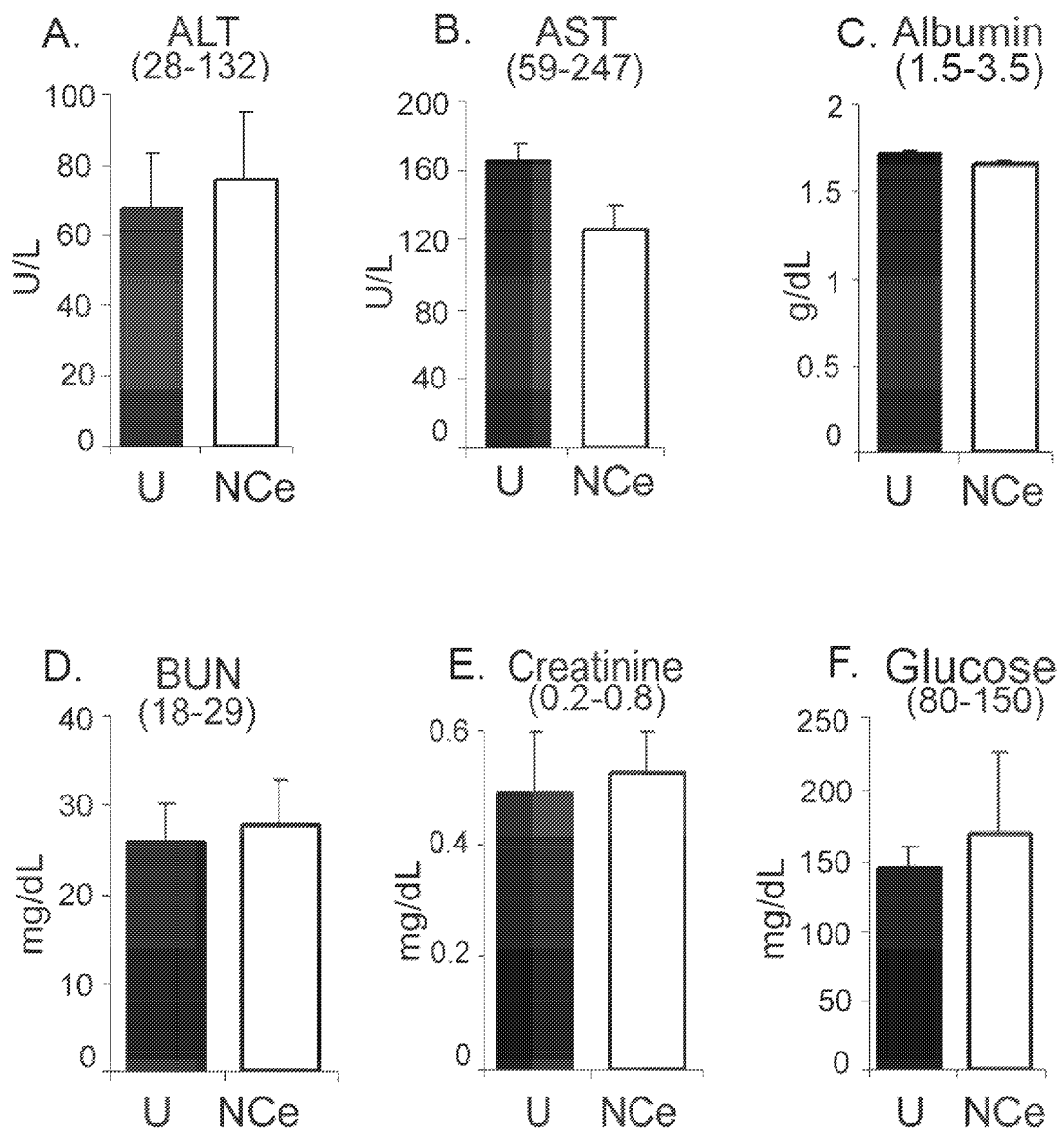
FIG. 5: NCe treatment is non-toxic in nude mice. After sacrificing animal groups (n=6) at the end of the study (day 30), blood was collected in heparin coated tubes and plasma was prepared. A panel of liver and kidney cytotoxic tests were performed in plasma prepared from control and NCe treated mice as per the manufacturer's instructions, A. ALT (Alanine Transaminase), B. AST (Aspartate Transaminase), C. Albumin, D. BUN (Blood Urea Nitrogen), E. Creatinine and F. Glucose.

NCe Treatment is Nontoxic In Vivo:

We further examined the cellular toxicity of NCe in vivo. Various organs (liver heart, spleen, kidney and lungs) were excised from untreated and NCe treated mice at the end of the study, formalin fixed and processed for obtaining section slides. H&E staining was performed on these sections and studied by a pathologist. The morphological architectural structure of all organs from treated and untreated mice appeared to be normal and no necrosis was observed (FIG. 11A-E; 100×). Further, plasma was separated from blood collected in heparin coated tubes and analyzed for liver function tests (aspartate aminotransferase, AST; alanine aminotransferase, ALT; albumin) and kidney function tests (creatinine; blood urea nitrogen, BUN; albumin). No significant difference was observed between the untreated and NCe treated mice and all values were found within the normal limits in both groups (FIG. 5A-E). No fluctuation in the glucose levels was observed either (FIG. 5F). These data show that NCe treatment on every third day for 4 weeks at the dose of 0.1 mg/kg is safe and does not result in tissue cytotoxicity or any abnormal physiological vital functions.

Figure 6:
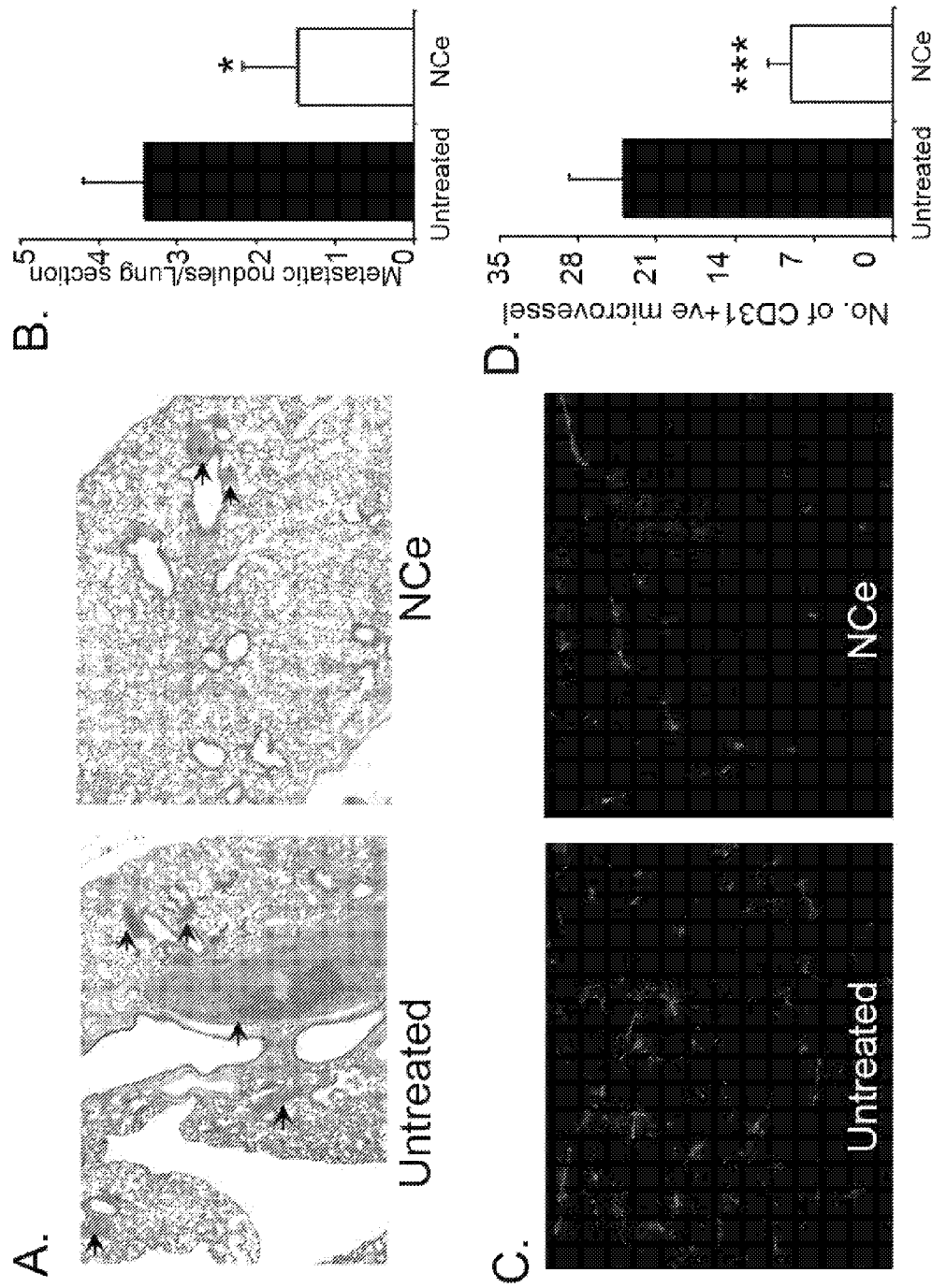
FIG. 6: NCe inhibits metastasis and vessel formation in A2780 xenografts. A. Representative H&E (×100) photomicrograph depicting lung metastatic nodules from Untreated and NCe treated mice (arrows point to metastatic nodules). B. Enumeration of metastatic nodules found per lung from Untreated and NCe treated mice. Total of 5 lung sections were observed to get the average count. *p<0.005 NCe compared to untreated. C. Representative photomicrograph of CD31 staining of blood microvessels (×200) in A2780 xenografts at day 30. D. Count of average microvessels per high power field (×400) from five fields of three xenograft section from untreated and NCe treated mice. ***p<0.001, NCe treated to untreated.

NCe Inhibited Metastasis in Human A2780 Ovarian Carcinoma Cell Line Bearing Nude Mouse Model:

Since our in vitro data showed that NCe treatment inhibited growth factor induced migration and invasion, we further examined for the presence of metastasis in various organs. Microscopic study of H&E sections from various organs revealed no invasion of tumor cells inside liver, spleen and kidney (data not shown), although tumor nodules were visible on their surface of untreated mice. However, only metastasis observed was in lungs. Large metastatic nodules were observed in lungs of untreated mice, which were significantly reduced in lungs of NCe treated mice. FIG. 6A (40×) shows a representative photomicrograph of metastatic nodules in the lungs isolated from untreated and treated mice. Along with the reduction in size of the metastatic nodules, the number of nodules was also significantly decreased by NCe treatment (FIG. 6B), indicating that as observed in vitro (Fig.), NCe also restricted migration and invasion of tumors cells in vivo.

NCe Inhibited Angiogenesis in A2780 Ovarian Carcinoma Mouse Model:

As we did not observe any significant effect on cell proliferation or cell death in ovarian cancer cell lines in vitro but found significant reduction in tumor growth in vivo, we further investigated the underlying mechanism of NCe mediated reduction of tumor size. For this we focused on angiogenesis as it is one the important factors implicated in progression of ovarian cancer [26,27]. Also for a tumor to sustain, grow, proliferate and invade, formation of new vasculature is a prerequisite. Microvessel density of tumors increases in response to various angiogenic factors and the low oxygen availability in the growing tumors, which enables them to avoid death and proceed to invasion and metastasis. We evaluated the microvessel density by staining for CD31 in xenograft sections from A2780 bearing NCe treated and untreated mice. We found tumor treated with NCe exhibited significantly less number of CD31 positive microvessel as evident from the representative photomicrograph (FIG. 5C, 200×) and the quantification of positively stained vessels at high power read from 5 fields of five sections from each group (FIG. 5D, 400×). These indicate that NCe maybe targeting angiogenesis and as a consequence limiting tumor growth.

NCe Treatment Targets Angiogenesis by Inhibiting VEGF Signaling in Endothelial Cells:

VEGF is the most potent angiogenic factor that is produced by the tumor cells and is also overexpressed in ovarian tumors [28,29,30]. To investigate if NCe treatment maybe restricting angiogenesis by inhibiting VEGF production/levels, we examined the effect of NCe on VEGF production in SKOV3 cells in vitro. SKOV3 cells were grown, kept in serum free conditions overnight and treated with EGF to stimulate VEGF production. Post 24 h supernatant was used to estimate the levels of VEGF by ELISA. As shown in FIG. 12A, treatment with EGF induced the production of VEGF in SKOV3 cells, while no changes were found in VEGF levels when cells were treated with NCe. Under similar experimental conditions we also estimated the levels of IL-8, which is involved in ovarian cancer pathogenesis and VEGF production [31]. Similar to VEGF, NCe did not affect the levels of IL18 production (FIG. 12B). As a further confirmation, we also immuno-stained for VEGF levels in the A2780 xenografts from NCe treated and untreated mice and observed no change in the VEGF expression (FIG. 12C). All these findings clearly suggest that NCe does not modulate the VEGF levels in ovarian cancer cells (or other cytokines) but limits angiogenesis by some other mechanism.

Figure 7:
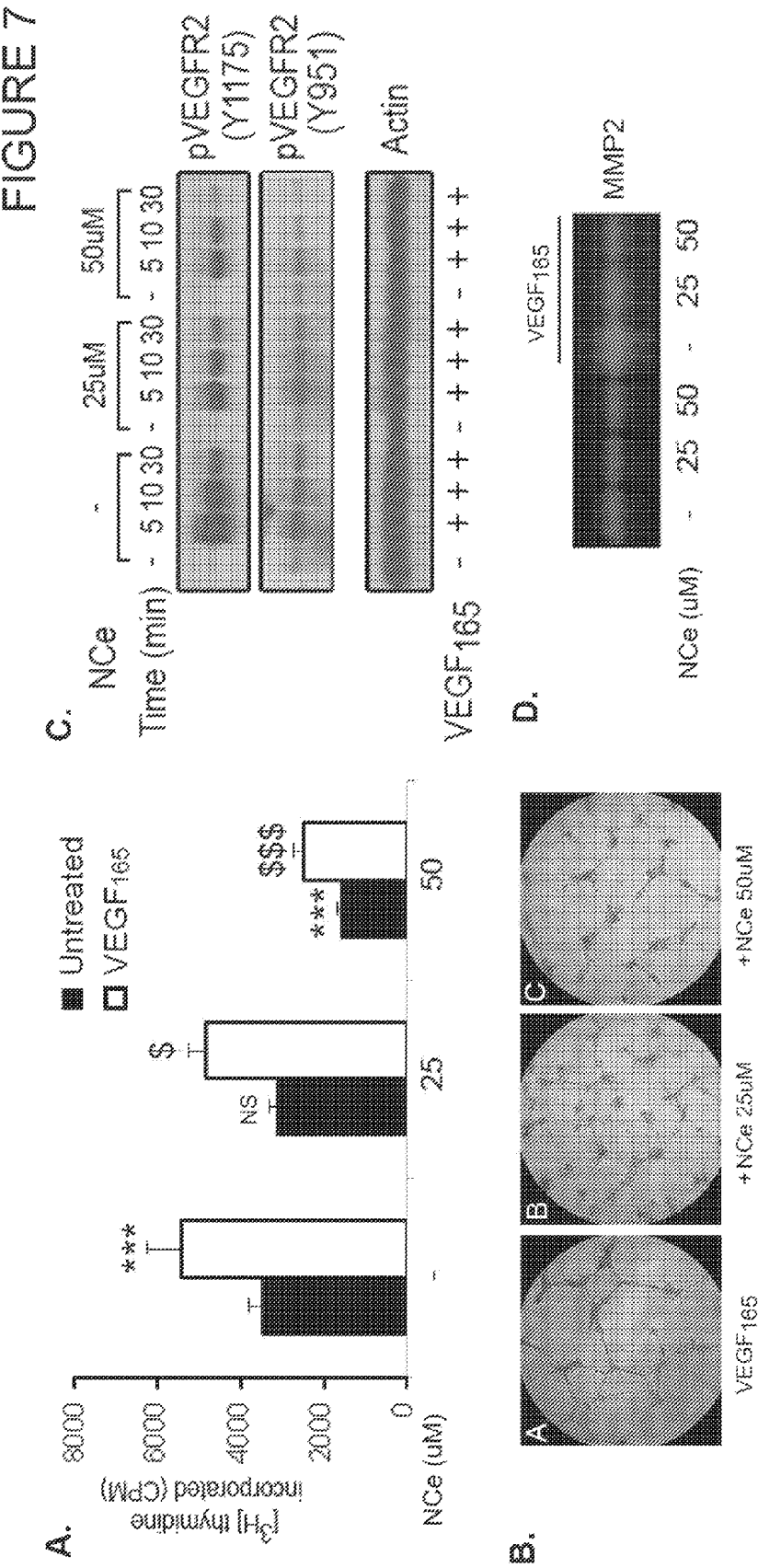
FIG. 7: NCe treatment inhibits VEGF induced downstream signaling in endothelial cells. A. HUVEC cells were treated with indicated concentrations of NCe and VEGF. DNA synthesis was measured by [$^3$H]-thymidine incorporation (n=4). ***, p<0.001; NS not significant compare with untreated cells. $, p<0.05; $$$, p<0.001 compared with VEGF treated cells. B. To examine the effect of NCe on tube formation in HUVEC cells, matrigel matrix was uniformly plated onto 8-well chamber slides (0.15 ml) and incubated at 37° C. for 30 min. During the incubation time, HUVEC cells in T75 flasks were washed with PBS and digested with 1× trypsin solution for about 3 min, and suspended in growth factors free medium. The cells were counted and diluted to $2\times10^5$/ml in medium. To set up the tube formation assay, cells were treated with NCe (25-50 μM) was mixed with cells in the presence or absence of VEGF165 (25 ng/ml) and transferred to each well (200 μl) coated with matrigel. The plates or slides were incubated at 37° C. for 16 h and imaged under a phase contrast inverted microscope at 10× objective magnification. C. To examine the effect of NCe treatment on VEGF induced phosphorylation of VEGFR2 (Y1175 and Y951) serum-starved HUVECs were treated with or without NCe (25-50 μM) and then stimulated with 25 ng/ml VEGF for 5-30 minutes. Immunoblotting was performed with pVEGFR2 (Y1175) and actin antibodies for protein loading control. D. To evaluate the effect of NCe on VEGF induced MMP2 activity, HUVEC cells were treated with NCe (25-50 μM) in the presence or absence of VEGF165 (25 ng/ml). Post 24 h of incubation, cell supernatant was processed for zymography assay as described in methods.

Since NCe treatment significantly reduced the number of microvessels in treated tumor without affecting the VEGF expression, we wanted to investigate if NCe modulates angiogenesis signaling downstream of VEGF in endothelial cells. For this, we examined the effect of NCe on VEGF mediated signaling on HUVEC endothelial cells. First, we observed for the effect of NCe on VEGF induced proliferation of HUVEC cells by thymidine incorporation, which was significantly attenuated by NCe treatment (FIG. 7A). The next step for proliferating endothelial cells is to form new vessels. HUVEC cells ($2 \times 10^4$) were plated on matrigel coated 96 well plate in the presence of NCe (25-50 μM) with or without $VEGF_{165}$ (25 ng/ml) as angiogenic stimuli. Morphology of the cells in matrigel was examined after 18 h of incubation under an inverted microscope to observe for tube formation. $VEGF_{165}$ induced endothelial tube formation was significantly retarded by NCe treatment (FIG. 7B). NCe treatment also reduced the phosphorylation of VEGFR2 at Tyr1175 in HUVEC cells in response to VEGF165 treatment (FIG. 7C), which is critical for proliferation and the recruitment of adaptor proteins including p85 of PI3Kinase and PLCγ [32]. It also attenuated phosphorylation of VEGFR2 at Y951, which is an autophosphorylation site that leads to recruitment of adaptor proteins, including Shc, Grb2, PI-3 kinase, Nck and the protein tyrosine phosphatases SHP-1 and SHP-2 [33]. NCe also inhibited VEGF induced MMP2 activity in endothelial cells as determined by zymography assay (FIG. 7D). These data clearly suggest that NCe treatment inhibits VEGF mediated downstream signaling in endothelial cells and as a result may interfere with proliferation and survival of endothelial cells.

Figure 8:
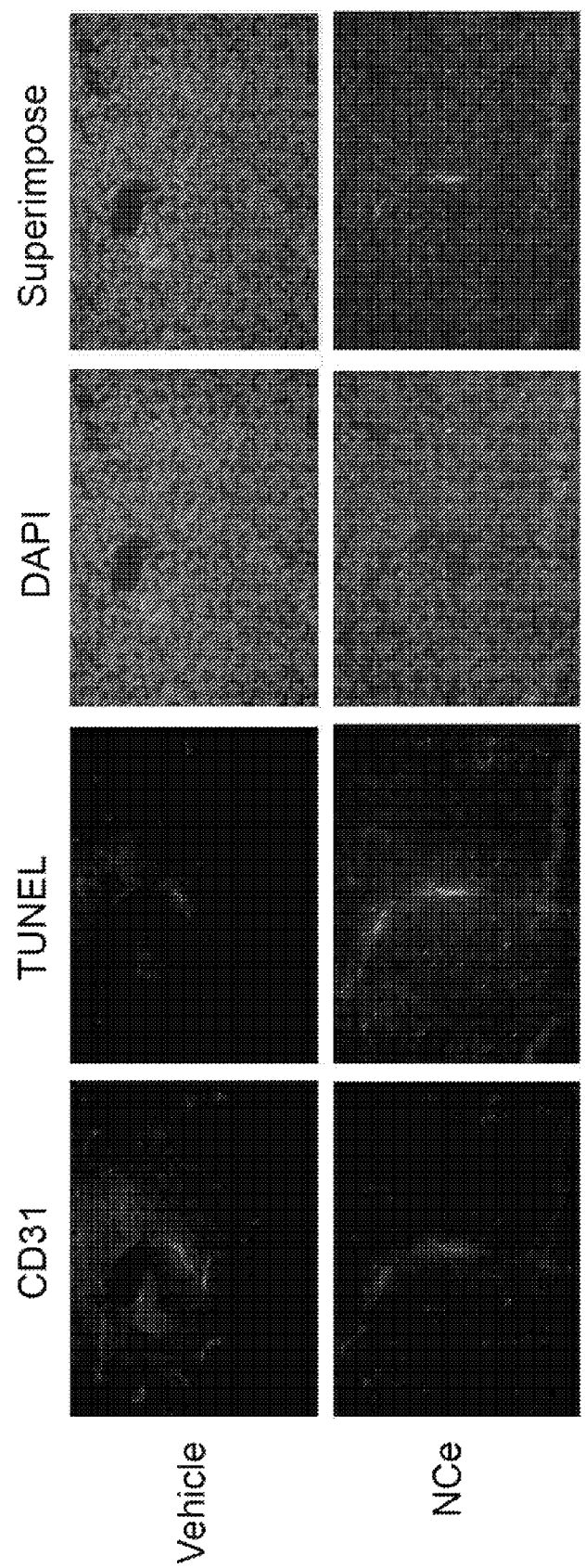
FIG. 8: NCe treatment potentiates the endothelial apoptosis of ovarian tumor in vivo. Double of staining CD31 and TUNEL was performed as described in methods. First panel depicts CD31-FITC labeled endothelial cells as part of a microvessel (red). Second panel depicts the same microvessel stained positive for apoptotic marker TUNEL labeled with FITC (green). Third panel shows blue nuclei stained with DAPI, indicating presence of tumor cells. The last panel shows merged image of all first three panels. The microvessel appears yellowish due to co-localization of CD31 and TUNEL.
Figure 9:
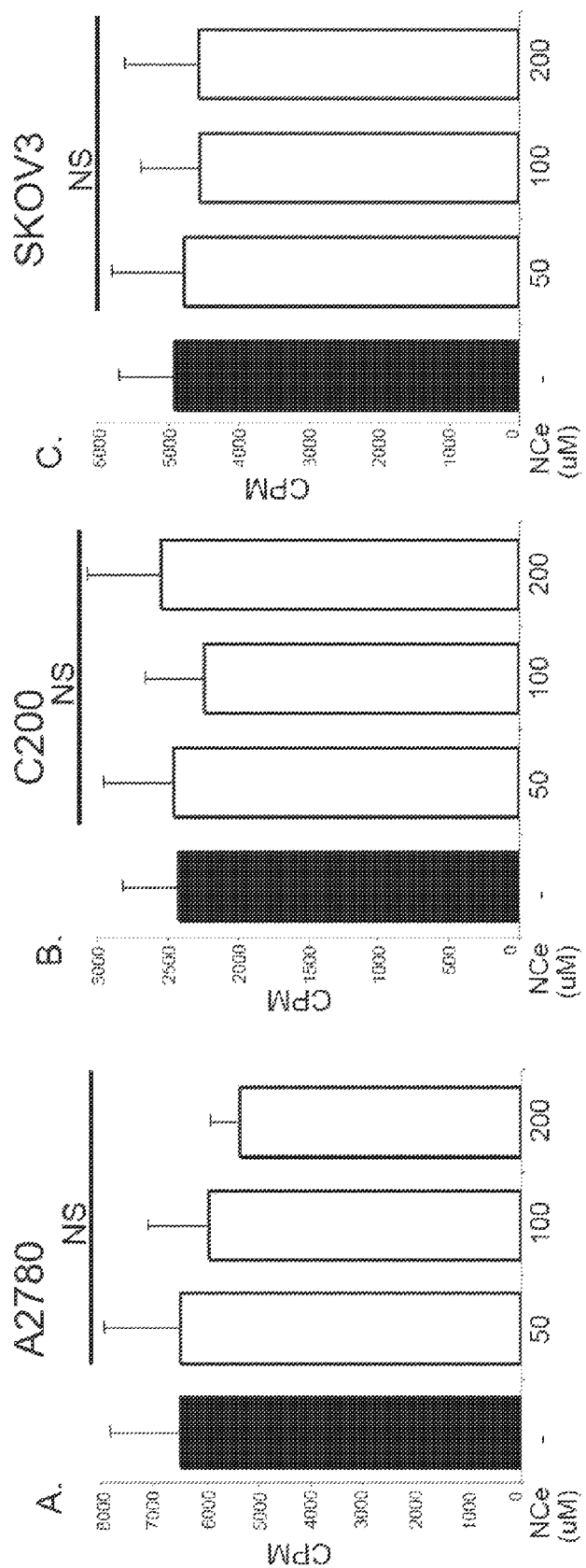
FIG. 9: NCe has no effect on cell proliferation of ovarian cancer cell lines. $5\times10^4$ cells of A. A2780, B. C200 and C. SKOV3 were plated in 24 wells, treated with indicated doses of NCe for 72 h, followed by exposure to [3H]-thymidine for 6 h and subsequent radioactive counts. The data is representation of three separate experiments done in triplicates. NS, non-significant compared with control.
Figure 10:
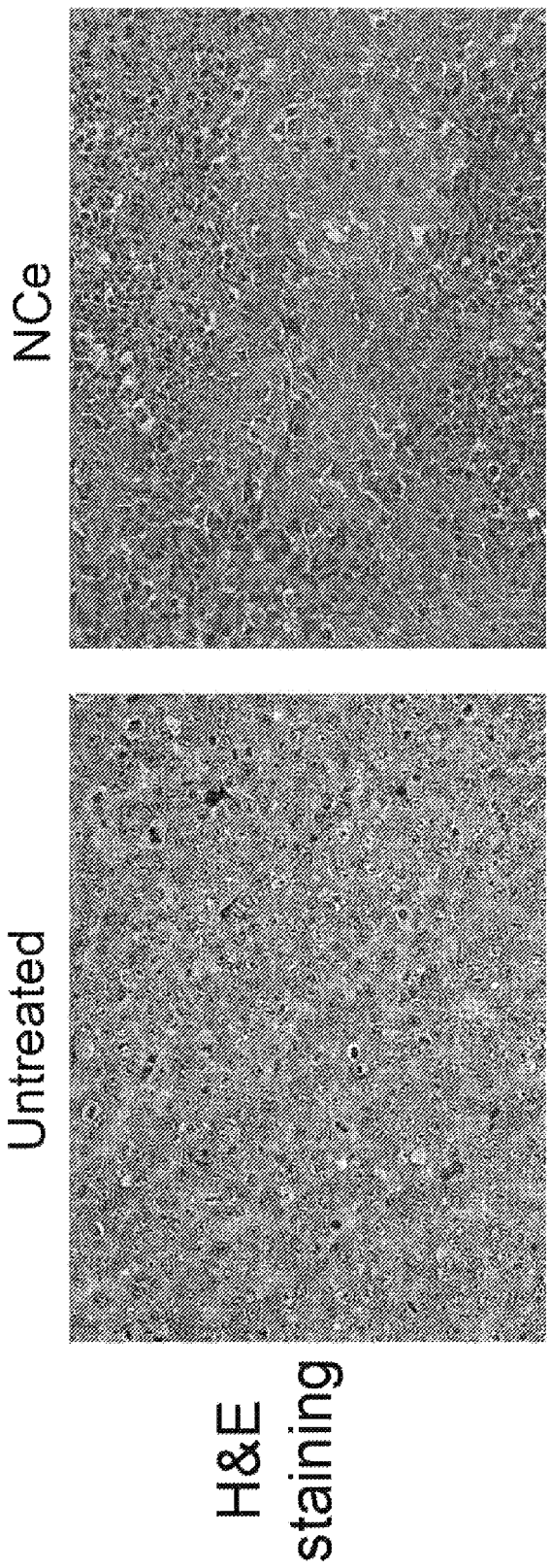
FIG. 10: Xenografts. Provides a representative photomicrograph of H&E staining (200×) of A2780 xenografts at day 30.
Figure 11:
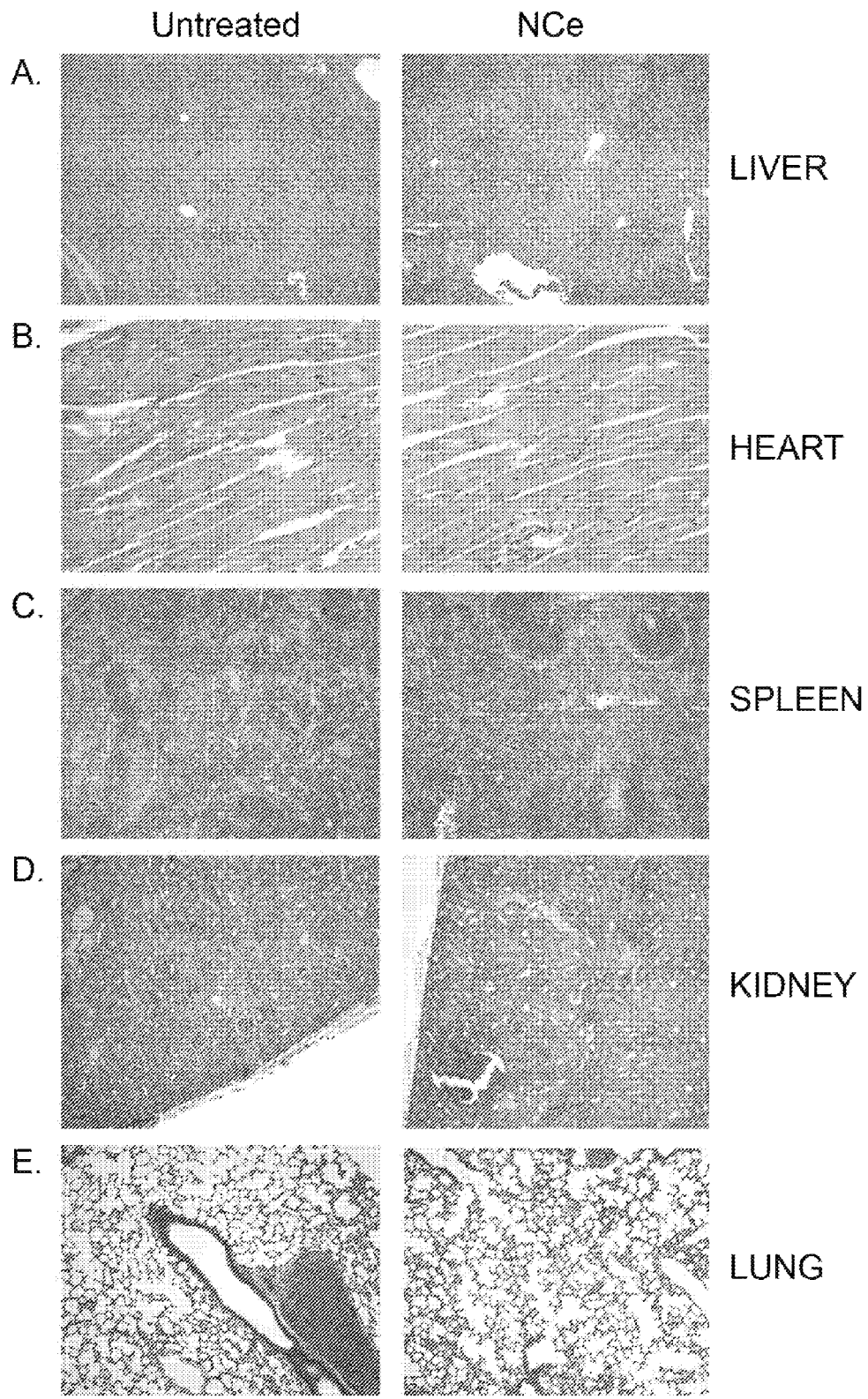
FIG. 11: NCe treatment is non-toxic in nude mice bearing human A2780 carcinoma. After sacrificing animal groups, organs of five mice from each group were formalin fixed, processed for histological sectioning and stained with H&E to observe morphology of the tissue. Representative photomicrographs (100×) of A. Liver; B. Heart; C. Spleen; D. Kidney and E. lungs, show normal morphological architecture in tissues of both untreated and NCe treated mice.

NCe Treatment Specifically Targets Endothelial Cells In Vivo:

To investigate if NCe has inhibitory effect on vessel formation in vivo as observed in vitro, we performed double staining with CD31 and TUNEL in the xenograft slides from both treated and untreated mouse groups. As shown in FIG. 8, CD31 recognized endothelial cells in the microvessels (stained red, first panel). Cells undergoing apoptosis were detected by performing TUNEL staining (stained green, second panel). Upon superimposing, it was observed that TUNEL and CD31 stains were colocalized (yellowish, last panel), indicating that it was the endothelial cells specifically in the microvessels that were undergoing apoptosis under NCe treatment. These data suggest a potential role for NCe as an anti-angiogenic molecule that acts by targeting endothelial cells and VEGF signaling.

Discussion

The science of developing nanoparticles into nanomedicine to encounter human diseases for better health outcomes is a rapidly progressing field. A number of metal nanoparticles have been designed and shown to be of therapeutic interest in various animal models, especially in the field of cancer [34,35]. Successful incorporation of nanoparticles as anti-cancer therapeutics can open an entirely new avenue for cancers like ovarian, where chemotherapeutic options are limited and high mortality is a serious concern. In this regard we investigated the potential of a unique cerium oxide nanoparticles, (nanoceria; NCe) as a therapeutic agent in ovarian cancer.

In the present study, we show for the first time that NCe has the potential to inhibit ovarian tumor growth and metastasis. We show that NCe attenuated basal levels of oxidative stress, invasion and migration of ovarian cancer cells without modulating their cell growth. It also significantly attenuated tumor growth in A2780 bearing nude mice when given intraperitoneally. Our study found a novel property of NCe as anti-angiogenic as its treatment reduced the microvessel density in ovarian xenografts, inhibited proliferation and induced apoptosis in endothelial cells in vitro and in vivo respectively, and also attenuated VEGF mediated downstream signaling in HUVEC. In vivo treatment of NCe resulted in specific apoptosis of endothelial cells in the microvessels being formed in the tumor tissue. Overall, our study presents novel property of NCe as an anti-angiogenic agent for its use in ovarian cancer.

The most attractive property of cerium oxide nanoparticles is their capacity to serve as free radical scavengers to provide protection against chemical, biological, and radiological insults that promote the production of free radicals [3,4,5]. NCe offers many active sites for free radical scavenging due to its large surface/volume ratio and mixed valence states (+4 and +3) for unique redox chemistry. Moreover, its unique regenerative property ($Ce^{3+}$—$Ce^{4+}$—$Ce^{3+}$) [4] makes NCe long-lived and can confer their beneficial effect for extended periods of time without redosing. It is reported recently NCe selectively conferred radioprotection to the normal cells (CRL 8798) against ROS compared to the breast cancer cells [5]. It also confers radioprotection against pneumonitis and gastrointestinal epithelium by reducing ROS [36,37]. Another recent study showed NCe to bestow protection from monocrotaline-induced hepatoxicity due to oxidative stress [38]. Our finding showed that NCe acts as an anti-oxidant in ovarian cancer is in agreement with these previous reports. However, NCe has been shown to induce oxidative stress in other cancer cell lines including human bronchoalveolar carcinoma derived cell line (A549) and squamous SCL-1 tumor cell line [39]. These reports suggest that cerium oxide particles may have differential anti-oxidant properties dependent on the nature of cell type. In our study, although the anti-oxidant property of NCe was able to reduce basal levels of oxidative stress but failed to inhibit proliferation of ovarian cancer cell lines in vitro. Interestingly, NCe inhibited growth factor induced migration and invasion of ovarian cancer cell lines. Similar to our observation, Tarnuzzer et al [5] also found non-cytotoxic effect of NCe on MCF7 breast cancer cell line. However, polymer-coated NCe showed cytotoxic effect on squamous tumor SCL-1 cells [39]. The discrepancy between our and other [39] reports may be due to any change in surface properties of nanoparticles in various cell types the difference between the preparation and nature of nanoparticles and cell type.

On observing that NCe treatment inhibited GF induced migration/invasion in vitro, we examined its ability to modulate tumor growth in vivo. We found that administration of NCe (0.1 mg/kgbdwt) on every third day significantly retarded A2780 xenograft growth in vivo which was also accompanied by attenuation of metastatic nodule size and number in lung. This is the first report that demonstrates the in vivo ability of NCe to inhibit ovarian tumor growth and metastasis. Also, this dose of NCe is well tolerated by mice without any cytotoxic or adverse physiological effects observed in the vital organs. These findings are in agreement of previous report where NCe upto 135 mg/kg body weight did not cause any death or notable side effect in nude mice with normal pathology of vital organs [36]. However, a recent report indicates the toxic effect of NCe in rodents [40]. This can be accounted for as the dose of NCe used in the previous study is 1000-2500 times higher (100-250 mg/kg body weight) then what we have used in our study (0.1 mg/kg body weight) [40].

Although in vitro, NCe treatment did not affect ovarian cancer cell growth, but we observed lesser staining of Ki-67, a maker of cell proliferation, suggesting NCe treatment might be affecting the tumor micro-environment rather than having a direct effect on tumor cells. To determine the mechanism by which NCe maybe restricting tumor growth, we examined the microvessel density in treated and untreated tumor and found a significant reduction in NCe treated tumor as evident from CD31 staining, a marker for endothelial cells. Interestingly, NCe did not modulate the production of VEGF production in vitro and in vivo. These observations led us to hypothesize that NCe maybe specifically targeting the endothelial cells responsible for formation of new vessels.

Angiogenesis is important for tumor development and growth and VEGF has been shown to be a major angiogenesis inducer primarily through the VEGF type 2 receptor (VEGFR2) [41,42]. VEGF binding initiates autophosphorylation of VEGFR2, which, in turn, creates docking sites for Src homology domain 2-containing adaptor molecules. This event is followed by activation of diverse key angiogenic enzymes including MMP2. We observed that NCe treatment inhibited VEGF induced proliferation, capillary tube formation and MMP2 activation in endothelial cells. NCe treatment attenuated VEGF mediated phosphorylation of VEGFR2 (Y1175 and Y951), a prerequisite for VEGF to signal to endothelial cells. Phosphorylation of VEGFR2 (Y1175) is critical for endothelial proliferation and the recruitment of adaptor proteins including p85 of PI3Kinase and PLCγ [32] and phosphorylation of VEGFR2 at Y951 is important for recruitment of adaptor proteins [33]. Inhibition of VEGF induced downstream signaling including proliferation, tube formation and MMP2 activation by NCe treatment indicating a novel anti-angiogenic property of NCe. Targeting of endothelial cells by NCe in vivo was also supported TUNEL assay in NCe treated xenografts specific to CD31+ve endothelial cells. The role of oxidative stress in angiogenesis is an emerging area of investigation [43]. An anti-angiogenic property of NCe might be modulating VEGF mediated signaling events which are redox sensitive [42]. This is the first report demonstrating any cerium oxide nanoparticles to exhibit an anti-angiogenic property with specificity for endothelial cells.

Anti-angiogenic agents have demonstrated activity in terms of both response and progressive free survival (PFS) in phase II and phase III clinical trials for women with epithelial ovarian cancer, both in the front-line and relapsed setting [44, 45, 46, 47]. But recent emerging reports indicate the therapy to be associated with increased fatal reactions [48, 49, 50, 51]. Therefore, novel strategies and agents that can target angiogenesis without many side effects are still required.

Taken together, our results reveal a new role of cerium oxide nanoparticles as a novel, non-toxic anti-angiogenic agent which restricted ovarian tumor growth in preclinical mouse model of ovarian cancer. Our study opens up a new avenue of using nanoparticles as feasible therapeutics in ovarian cancer. A future option to increase the efficacy and specificity of NCe can be conjugating it with folic acid, a ligand for folate receptor over expressed in ovarian cancer, as a tool to deliver NCe specifically to tumor as a novel therapy. Moreover, NCe could be conjugated with other chemotherapeutic drugs for their specific delivery as well as enhancement of their cytotoxicity, while reducing the side effects. The outcome of these studies could open a new and novel avenue of therapy for ovarian cancer.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

REFERENCES

1. Bast R C, Jr., Urban N, Shridhar V, Smith D, Zhang Z, et al. (2002) Early detection of ovarian cancer: promise and reality. Cancer Treat Res 107: 61-97.
2. Friedlander M L (1998) Prognostic factors in ovarian cancer. Semin Oncol 25: 305-314.
3. Chen J, Patil S, Seal S, McGinnis J F (2006) Rare earth nanoparticles prevent retinal degeneration induced by intracellular peroxides. Nat Nanotechnol 1: 142-150.
4. Das M, Patil S, Bhargava N, Kang J F, Riedel L M, et al. (2007) Auto-catalytic ceria nanoparticles offer neuroprotection to adult rat spinal cord neurons. Biomaterials 28: 1918-1925.
5. Tarnuzzer R W, Colon J, Patil S, Seal S (2005) Vacancy engineered ceria nanostructures for protection from radiation-induced cellular damage. Nano Lett 5: 2573-2577.
6. Patil S, Sandberg A, Heckert E, Self W, Seal S (2007) Protein adsorption and cellular uptake of cerium oxide nanoparticles as a function of zeta potential. Biomaterials 28: 4600-4607.
7. Carmeliet P, Jain R K (2000) Angiogenesis in cancer and other diseases. Nature 407: 249-257.
8. Kerbel R, Folkman J (2002) Clinical translation of angiogenesis inhibitors. Nat Rev Cancer 2: 727-739.
9. Ferrara N (1996) Vascular endothelial growth factor. Eur J Cancer 32A: 2413-2422.
10. Macchiarini P, Fontanini G, Hardin M J, Squartini F, Angeletti C A (1992) Relation of neovascularisation to metastasis of non-small-cell lung cancer. Lancet 340: 145-146.
11. Paley P J, Staskus K A, Gebhard K, Mohanraj D, Twiggs L B, et al. (1997) Vascular endothelial growth factor expression in early stage ovarian carcinoma. Cancer 80: 98-106.
12. Weidner N, Carroll P R, Flax J, Blumenfeld W, Folkman J (1993) Tumor angiogenesis correlates with metastasis in invasive prostate carcinoma. Am J Pathol 143: 401-409.
13. Weidner N, Semple J P, Welch W R, Folkman J (1991) Tumor angiogenesis and metastasis—correlation in invasive breast carcinoma. N Engl Med 324: 1-8.
14. Burger R A, Sill M W, Monk B J, Greer B E, Sorosky J I (2007) Phase II trial of bevacizumab in persistent or recurrent epithelial ovarian cancer or primary peritoneal cancer: a Gynecologic Oncology Group Study. J Clin Oncol 25: 5165-5171.
15. Narita K, Staub J, Chien J, Meyer K, Bauer M, et al. (2006) HSulf-1 inhibits angiogenesis and tumorigenesis in vivo. Cancer Res 66: 6025-6032.

16. Rattan R, Giri S, Hartmann L C, Shridhar V (2011) Metformin attenuates ovarian cancer cell growth in an AMP-kinase dispensable manner. J Cell Mol Med 15: 166-178.
17. Rattan R, Giri S, Singh A K, Singh I (2005) 5-Aminoimidazole-4-carboxamide-1-beta-D-ribofuranoside inhibits cancer cell proliferation in vitro and in vivo via AMP-activated protein kinase. J Biol Chem 280: 39582-39593.
18. Giri S, Khan M, Nath N, Singh I, Singh A K (2008) The role of AMPK in psychosine mediated effects on oligodendrocytes and astrocytes: implication for Krabbe disease. J Neurochem 105: 1820-1833.
19. Giri S, Khan M, Rattan R, Singh I, Singh A K (2006) Krabbe disease: psychosine-mediated activation of phospholipase A2 in oligodendrocyte cell death. J Lipid Res 47: 1478-1492.
20. Malinda K M, Sidhu G S, Mani H, Banaudha K, Maheshwari R K, et al. (1999) Thymosin beta4 accelerates wound healing. J Invest Dermatol 113: 364-368.
21. Rattan R, Graham R P, Maguire J L, Giri S, Shridhar V (2011) Metformin suppresses ovarian cancer growth and metastasis with enhancement of cisplatin cytotoxicity in vivo. Neoplasia In Press.
22. Chan D W, Liu V W, Tsao G S, Yao K M, Furukawa T, et al. (2008) Loss of MKP3 mediated by oxidative stress enhances tumorigenicity and chemoresistance of ovarian cancer cells. Carcinogenesis 29: 1742-1750.
23. Liu L Z, Hu X W, Xia C, He J, Zhou Q, et al. (2006) Reactive oxygen species regulate epidermal growth factor-induced vascular endothelial growth factor and hypoxia-inducible factor-1 alpha expression through activation of AKT and P70S6K1 in human ovarian cancer cells. Free Radic Biol Med 41: 1521-1533.
24. Xia C, Meng Q, Liu L Z, Rojanasakul Y, Wang X R, et al. (2007) Reactive oxygen species regulate angiogenesis and tumor growth through vascular endothelial growth factor. Cancer Res 67: 10823-10830.
25. Miyamoto S, Yagi H, Yotsumoto F, Horiuchi S, Yoshizato T, et al. (2007) New approach to cancer therapy: heparin binding-epidermal growth factor-like growth factor as a novel targeting molecule. Anticancer Res 27: 3713-3721.
26. Gomez-Raposo C, Mendiola M, Barriuso J, Casado E, Hardisson D, et al. (2009) Angiogenesis and ovarian cancer. Clin Transl Oncol 11: 564-571.
27. Markman M (2009) Antiangiogenic drugs in ovarian cancer. Expert Opin Pharmacother 10: 2269-2277.
28. Lose F, Nagle C M, O'Mara T, Batra J, Bolton K L, et al. (2010) Vascular endothelial growth factor gene polymorphisms and ovarian cancer survival. Gynecol Oncol 119: 479-483.
29. Mesiano S, Ferrara N, Jaffe R B (1998) Role of vascular endothelial growth factor in ovarian cancer: inhibition of ascites formation by immunoneutralization. Am J Pathol 153: 1249-1256.
30. Tempfer C, Obermair A, Hefler L, Haeusler G, Gitsch G, et al. (1998) Vascular endothelial growth factor serum concentrations in ovarian cancer. Obstet Gynecol 92: 360-363.
31. Xu L, Fidler I J (2000) Interleukin 8: an autocrine growth factor for human ovarian cancer. Oncol Res 12: 97-106.
32. Takahashi T, Yamaguchi S, Chida K, Shibuya M (2001) A single autophosphorylation site on KDR/Flk-1 is essential for VEGF-A-dependent activation of PLC-gamma and DNA synthesis in vascular endothelial cells. Embo J 20: 2768-2778.
33. Kroll J, Waltenberger J (1997) The vascular endothelial growth factor receptor KDR activates multiple signal transduction pathways in porcine aortic endothelial cells. J Biol Chem 272: 32521-32527.
34. Bharali D J, Mousa S A (2010) Emerging nanomedicines for early cancer detection and improved treatment: current perspective and future promise. Pharmacol Ther 128: 324-335.
35. Seigneuric R, Markey L, Nuyten D S, Dubernet C, Evelo C T, et al. (2010) From nanotechnology to nanomedicine: applications to cancer research. Curr Mol Med 10: 640-652.
36. Colon J, Herrera L, Smith J, Patil S, Komanski C, et al. (2009) Protection from radiation-induced pneumonitis using cerium oxide nanoparticles. Nanomedicine 5: 225-231.
37. Colon J, Hsieh N, Ferguson A, Kupelian P, Seal S, et al. (2010) Cerium oxide nanoparticles protect gastrointestinal epithelium from radiation-induced damage by reduction of reactive oxygen species and upregulation of superoxide dismutase 2. Nanomedicine 6: 698-705.
38. Amin K A, Hassan M S, Awad el S T, Hashem K S (2011) The protective effects of cerium oxide nanoparticles against hepatic oxidative damage induced by monocrotaline. Int J Nanomedicine 6: 143-149.
39. Alili L, Sack M, Karakoti A S, Teuber S, Puschmann K, et al. (2011) Combined cytotoxic and anti-invasive properties of redox-active nanoparticles in tumor-stroma interactions. Biomaterials.
40. Hardas S S, Butterfield D A, Sultana R, Tseng M T, Dan M, et al. (2010) Brain distribution and toxicological evaluation of a systemically delivered engineered nanoscale ceria. Toxicol Sci 116: 562-576.
41. Folkman J (1971) Tumor angiogenesis: therapeutic implications. N Engl J Med 285: 1182-1186.
42. Matsumoto T, Claesson-Welsh L (2001) VEGF receptor signal transduction. Sci STKE 2001: re21.
43. Ushio-Fukai M, Nakamura Y (2008) Reactive oxygen species and angiogenesis: NADPH oxidase as target for cancer therapy. Cancer Lett 266: 37-52.
44. Burger R A Overview of anti-angiogenic agents in development for ovarian cancer. Gynecol Oncol.
45. Cannistra S A, Matulonis U A, Penson R T, Hambleton J, Dupont J, et al. (2007) Phase II study of bevacizumab in patients with platinum-resistant ovarian cancer or peritoneal serous cancer. J Clin Oncol 25: 5180-5186.
46. Garcia A A, Hirte H, Fleming G, Yang D, Tsao-Wei D D, et al. (2008) Phase II clinical trial of bevacizumab and low-dose metronomic oral cyclophosphamide in recurrent ovarian cancer: a trial of the California, Chicago, and Princess Margaret Hospital phase II consortia. J Clin Oncol 26: 76-82.
47. Penson R T, Dizon D S, Cannistra S A, Roche M R, Krasner C N, et al. Phase II study of carboplatin, paclitaxel, and bevacizumab with maintenance bevacizumab as first-line chemotherapy for advanced mullerian tumors. J Clin Oncol 28: 154-159.
48. Bansal N, Hoffman M (2011) Bladder perforation in a patient with recurrent epithelial ovarian cancer after treatment with bevacizumab. Gynecol Oncol 120: 313-314.
49. Koskas M, Chereau E, Ballester M, Selle F, Rouzier R, et al. (2010) Wound complications after bevacizumab treatment in patients operated on for ovarian cancer. Anticancer Res 30: 4743-4747.
50. Lecarpentier E, Ouaffi L, Mir O, Berveiller P, Maurel M, et al. (2010) Bevacizumab-induced small bowel perforation in a patient with breast cancer without intraabdominal metastases. Invest New Drugs.
51. Randall L M, Monk B J Bevacizumab toxicities and their management in ovarian cancer. Gynecol Oncol 117: 497-504.

That which is claimed:

1. A method of treating ovarian cancer in a mammal, the method comprising parenteral administration to the mammal of an effective amount of cerium oxide in nanoparticles having a predominance of $Ce^{+3}$.

2. The method of claim 1, wherein the mammal is a human subject.

3. The method of claim 1, wherein parenteral administration comprises intraperitoneal administration.

4. The method of claim 1, wherein the effective amount comprises less than approximately 1 mg per kilogram of body weight of the mammal.

5. The method of claim 1, wherein the effective amount comprises approximately 0.1 mg per kilogram of body weight of the mammal.

6. The method of claim 1, wherein the effective amount is parenterally administered approximately every 72 hours.

7. A method of inhibiting growth-mediated cell migration and invasion of mammalian ovarian cancer cells, the method comprising contacting the cells with an effective amount of cerium oxide nanoparticles having a predominance of $Ce^{+3}$.

8. A method of inhibiting angiogenesis associated with a mammalian ovarian carcinoma, the method comprising contacting the carcinoma with an effective amount of cerium oxide nanoparticles having a predominance of $Ce^{+3}$.

9. The method of claim 8, wherein contacting the carcinoma further comprises contacting vascular endothelial cells associated with the carcinoma.

* * * * *